(12) United States Patent
Ookawa

(10) Patent No.: US 9,322,790 B2
(45) Date of Patent: Apr. 26, 2016

(54) X-RAY INSPECTION DEVICE

(75) Inventor: Naonobu Ookawa, Shizuoka-ken (JP)

(73) Assignee: Yamaha Hatsudoki Kabushiki Kaisha, Shizuoka-ken (JP)

( * ) Notice: Subject to any disclaimer, the term of this patent is extended or adjusted under 35 U.S.C. 154(b) by 156 days.

(21) Appl. No.: 14/371,678

(22) PCT Filed: Jun. 27, 2012

(86) PCT No.: PCT/JP2012/004174
§ 371 (c)(1),
(2), (4) Date: Jul. 10, 2014

(87) PCT Pub. No.: WO2013/105149
PCT Pub. Date: Jul. 18, 2013

(65) Prior Publication Data
US 2014/0334605 A1    Nov. 13, 2014

(30) Foreign Application Priority Data

Jan. 12, 2012    (JP) ................. 2012-004380

(51) Int. Cl.
| | |
|---|---|
| *G01N 23/04* | (2006.01) |
| *H05K 13/08* | (2006.01) |
| *G01T 7/08* | (2006.01) |
| *H05K 3/34* | (2006.01) |

(52) U.S. Cl.
CPC .............. *G01N 23/04* (2013.01); *G01N 23/043* (2013.01); *G01T 7/08* (2013.01); *H05K 13/08* (2013.01); *G01N 2223/6113* (2013.01); *H05K 3/341* (2013.01); *H05K 2203/163* (2013.01)

(58) Field of Classification Search
CPC . G01V 5/0016; G01V 5/0066; G01V 5/0008; G01V 5/005; G01N 2223/639; G01N 23/046; G01N 2223/643; G01N 2223/3307; G01N 23/10
See application file for complete search history.

(56) References Cited

U.S. PATENT DOCUMENTS 5,541,856 A * 7/1996 Hammermeister .... G01N 23/16
324/501
5,754,621 A    5/1998 Suzuki et al.
(Continued)

FOREIGN PATENT DOCUMENTS

| CN | 1595124 A | 3/2005 |
|---|---|---|
| CN | 1898556 A | 1/2007 |

(Continued)

OTHER PUBLICATIONS

International Search Report; PCT/JP2012/004174; Sep. 25, 2012.
(Continued)

*Primary Examiner* — Hoon Song
(74) *Attorney, Agent, or Firm* — Studebaker & Brackett PC

(57) ABSTRACT

Provided is an X-ray inspection device having a pair of conveyor frames that is disposed symmetrically with respect to a center line as an axis along a substrate conveying direction, and clamps a printed substrate in a substrate width direction. A substrate conveying mechanism conveys in an X axis direction the printed substrate supported by the conveyor frames. A distance adjustment mechanism drives the pair of conveyor frames so that the conveyor frames approach or depart from each other in the Y axis direction, thereby adjusting the width dimension of a printed substrate that can be conveyed by the substrate conveying mechanism disposed on each of the conveyor frames.

4 Claims, 17 Drawing Sheets

(56) References Cited

U.S. PATENT DOCUMENTS

| | | | | |
|---|---|---|---|---|
| 5,836,504 A | * | 11/1998 | Koike | B23K 31/12 228/103 |
| 6,144,033 A | * | 11/2000 | Kokubu | B29D 30/0633 250/358.1 |
| 2005/0074088 A1 | * | 4/2005 | Ichihara | G01N 23/046 378/58 |
| 2005/0105682 A1 | * | 5/2005 | Heumann | G01N 23/046 378/58 |

FOREIGN PATENT DOCUMENTS

| | | |
|---|---|---|
| CN | 101963587 A | 2/2011 |
| EP | 0776151 A1 | 5/1997 |
| JP | 62-151268 A | 7/1987 |
| JP | 05-145226 A | 6/1993 |
| JP | 07-015176 A | 1/1995 |
| JP | 2002-189002 A | 7/2002 |
| JP | 2003-315288 A | 11/2003 |
| JP | 2004-028845 A | 1/2004 |
| JP | 2007-311497 A | 11/2007 |
| JP | 2008-066630 A | 3/2008 |
| KR | 10-0983244 B1 | 9/2010 |

OTHER PUBLICATIONS

The extended European search report issued by the European Patent Office on May 12, 2015, which corresponds to European Patent Application No. 12864997.7-1559 and is related to U.S. Appl. No. 14/371,678.

* cited by examiner

CLOSE UP POSITION

NON-CLOSE UP POSITION

X-RAY INSPECTION DEVICE

CROSS REFERENCE TO RELATED APPLICATIONS

This application claims benefit of priority to Japanese Patent Application 2012-004380 filed on Jan. 12, 2012, and to International Patent Application No. PCT/JP2012/004174 filed on Jun. 27, 2012, the entire content of each of which is incorporated herein by reference.

TECHNICAL FIELD

The present invention relates to an X-ray inspection device.

BACKGROUND

To inspect a printed substrate on which many electronic components are mounted, an X-ray inspection device using X-rays is known, as disclosed in Japanese Patent Application Laid-open No. 2003-315288 and Japanese Patent Application Laid-open No. 2002-189002. In such an X-ray inspection device, an inspection chamber is defined in a housing at which X-ray shielding processing has been performed to prevent exposure to X-rays, an X-ray source and an X-ray camera are installed in the inspection chamber, and X-rays are irradiated onto an inspection target (a printed substrate) and an X-ray image is captured using these devices. In order to carry a printed substrate into/out of the inspection chamber, a substrate table, to transfer the printed substrate on the substrate conveyor, is disposed in the housing.

Referring to FIG. 15, conveyor units 70P are disposed on a substrate table 60P, as disclosed in Japanese Patent Application Laid-open No. 2003-315288. The conveyor units 70P clamp a printed substrate W therebetween with respect to a substrate width direction (hereafter called "Y axis direction") which is orthogonal to the carry in/out direction of the printed substrate W (hereafter called "X axis direction"). Since a dimension in the Y axis direction of the target printed substrate W for inspection varies respectively, a width adjustment unit for adjusting the space between the conveyor units 70P is disposed on the substrate table 60P of Japanese Patent Application Laid-open No. 2003-315288. The width adjustment unit is configured by a fixed frame 71P which secures the conveyor units 70P to a base 61P of the substrate table 60P, and a movable frame 72P which is movable in the Y axis direction from the fixed frame 71P. When clamping a printed substrate W between the fixed frame 71P and the movable frame 72P, the movable frame 72P moves in the Y axis direction so as to adjust the dimension in the Y axis direction.

As the high integration of printed substrates are promoted in recent years, the use of transmission imaging where X-rays diagonally irradiated onto an essential inspection area at an elevation angle with respect to a plane of the printed substrate (called "oblique view capturing" in the present description), in addition to transmission imaging where X-rays, are irradiated in a normal line direction of the printed circuit (called "direct view imaging" in the present description), is increasingly demanded when X-ray transmission inspection is performed on a printed substrate.

In the case of a configuration of Japanese Patent Application Laid-open No. 2003-315288, where a plurality of types of printed substrates W are clamped using the fixed frame 71P and the movable frame 72P, the space for an opening required for transmitting X-rays increases if X-ray inspection is executed using both the oblique view capturing and the direct view imaging, which could increase the size of the entire apparatus.

FIGS. 16A-16D are comparative diagrams depicting a cross-sectional view of an X-ray inspection device in which an X-ray source (not illustrated) is disposed above, and an X-ray camera is movably disposed below. FIG. 16A and FIG. 16B are diagrams according to the present invention, and FIG. 16C and FIG. 16D are diagrams according to the prior art. FIG. 16C and FIG. 16D show a state when a substrate table 60P of Japanese Patent Application Laid-open No. 2003-315288 shown in FIG. 15, for example, is used, and the substrate table 60P is supported on a frame 111P having an opening 120 to transmit X-rays between the X-ray source and the X-ray camera 50.

In order to perform the oblique view capturing using the fixed frame 71P in FIG. 16C and FIG. 16D, a space d2, to transmit X-rays, must be secured in advance as indicated by d2 in FIG. 16C, hence the fixed frame 71P is disposed at a position where the opening of the base 61P is always blocked. Therefore if the oblique view capturing is not required, the fixed frame 71P gets in the way and limits the width of a printed substrate W, which is required for direct view imaging.

SUMMARY

With the foregoing in view, it is an object of the present invention to provide an X-ray inspection device that can eliminate unnecessary limitations when the oblique view capturing is used with the direct view imaging.

To solve this problem, the present invention provides an X-ray inspection device that is used on a conveyance path for conveying a printed substrate in a predetermined substrate conveying direction, having: a pair of conveyor frames configured to clamp the printed substrate with respect to a substrate width direction which is orthogonal to the substrate conveying direction in a horizontal plane; a pair of substrate conveyors, each substrate conveyor being disposed on the respective pair of the conveyor frames, the pair of substrate conveyors forming a substrate conveying mechanism configured to convey a printed substrate supported by the pair of conveyor frames in the substrate conveying direction; and a distance adjustment mechanism configured to drive the pair of conveyor frames so that each of the pairs of conveyor frames approaches or departs from each other in the substrate width direction, thereby adjusting a width dimension for allowing a printed substrate to be conveyed by the substrate conveying mechanism. In this aspect, a printed substrate clamped by a pair of conveyor frames is supported by the conveyor frames. The printed substrate supported by each conveyor frame is carried into the conveyor frame or carried out of the conveyor frame by a substrate conveying mechanism. The substrate conveying mechanism is formed by a pair of substrate conveyors disposed in the pair of conveyor frames respectively. Therefore the substrate conveying mechanism can adjust the width of a printed substrate that the substrate conveying mechanism is capable of carrying, by changing the space between the conveyor frames. Since the distance adjustment mechanism can adjust the space between the conveyor frames in the substrate width direction, various kinds of printed substrates can be supported within a range where the pair of conveyor frames can move. Here the distance adjustment mechanism drives the pair of conveyor frames so that each of the pair of conveyor frames approaches or departs from each other in the substrate width direction. This means that when a printed substrate which requires only the direct view imaging is held, even a printed substrate whose width dimension extends over the entire width of the opening can receive X-ray inspection. Moreover, the space is adjusted by moving the pair of conveyor frames respectively, hence the driving time can be reduced compared with a case when one of the conveyor frames is fixed and the other conveyor frame is movable.

In the X-ray inspection device, it is preferable that the distance adjustment mechanism drives the pair of conveyor frames such that the conveyor frames equally approach or depart from each other. In this aspect, the driving amount by each conveyor frame is equal, so the driving time can be decreased. Further, the center line that bisects the width of the printed substrate can be matched with the center position of the pair of conveyor frames in an approaching/departing direction. Hence in the case when an opening to transmit X-rays is disposed, centering with this opening is easier.

Preferably another mode further includes a frame having an opening to transmit X-rays, wherein the pair of conveyor frames is disposed on the frame symmetrically with respect to a center axis of the opening along the substrate conveying direction. In this aspect, the conveyor frames are disposed symmetrically with respect to the opening of the frame, and the distance adjustment mechanism drives each of the conveyor frames such that the conveyor frames equally approach or depart from each other along the substrate width direction, therefore each conveyor frame equally opens the opening in the printed substrate width direction while maintaining symmetry with respect to the center line of the opening along the substrate conveying direction. This means that the center line, that bisects the printed substrate width direction, can be matched with the center line of the opening, and therefore when the oblique view capturing is executed for a printed substrate held on the substrate table, the frame to support the substrate table can remain compact. Furthermore, a configuration to symmetrically move the pair of conveyor frames with respect to the frame is used. Hence the opening of the frame can be opened over the entire width. This means that when a printed substrate which requires only the direct view imaging is held, even a printed substrate whose width dimension extends over the entire width of the opening can receive X-ray inspection.

In the X-ray inspection device, it is preferable that the frame has four sides forming the opening of a square in planar view, and, out of the four sides, at least sides along the substrate conveying direction have a bevel inclining such that a downstream side in an X-ray irradiation direction of the X-ray irradiation unit is wider. In this aspect, the path of X-rays can be opened using the bevels when the oblique view capturing is performed, whereby the oblique view capturing becomes possible for a wider printed substrate.

In the X-ray inspection device, it is preferable that each of the pair of conveyor frames has a facing edge facing to each other with respect to the substrate width direction, and a bevel is formed on the facing edge, the bevel inclining such that a downstream side in an X-ray irradiation direction of the X-ray irradiation unit is wider. In this aspect, a wider effective opening diameter to transmit X-rays can be secured by the bevels, whereby the oblique view capturing becomes possible for an even wider printed substrate.

In the X-ray inspection device, it is preferable that the distance adjustment mechanism includes: double-end studs extending in the substrate width direction, screw directions of each double-ends stud at one end and at the other end being set to be opposite; a first nut mechanism installed in one of the conveyor frames, the first nut mechanism being screwed into one end of the double-end studs; a second nut mechanism installed in the other conveyor frame, the second nut mechanism being screwed into other end of the double-end studs; a motor configured to drive the double-end studs; and a power transfer unit configured to transfer power of the motor to both the double-end studs in a same direction at a same speed. In this aspect, if the double-end stud rotates in one direction (e.g. clockwise), the nut mechanisms screwed into the double-end studs transfer a force to the corresponding conveyor frames in directions for the conveyor frames to approach or depart from each other, and if the double-end studs rotate in the other direction (e.g. counterclockwise), the nut mechanisms screwed into the double-end studs transfer a force to the corresponding conveyor frames in directions to move the conveyor frames in the opposite directions from above. Therefore the pair of conveyor frames can be simultaneously driven using the single motor, whereby the drive system can be simplified and the number of components can be decreased.

In the X-ray inspection device, it is preferable that the substrate conveying mechanism further includes a conveyor driving mechanism configured to drive the pair of substrate conveyors, the conveyor driving mechanism includes a motor, a drive shaft being rotary-driven by the motor, and a first output pulley and a second output pulley being connected to the drive shaft, and the first output pulley and the second output pulley are connected with the drive shaft such that rotation of the first output pulley and the second output pulley are restricted but are movable with respect to an axis direction of the drive shaft, the first output pulley transferring power to one of the substrate conveyors and the second output pulley transferring power to the other substrate conveyor. In this aspect, the drive shaft is rotated by the rotation of the motor. The torque thereof is transferred to the substrate conveyors via the first and second output pulleys respectively. Therefore the substrate conveyors are simultaneously driven by the single motor in a same direction. The first output pulley and the second output pulley form a pair, so as to be movable in the axis direction of the drive shaft, in a state where rotation around the axis of the drive shaft is restricted respectively. Hence power can be transferred to each of the substrate conveyors without interrupting the displacement of the conveyor frames by the distance adjustment mechanism.

As described above, the present invention uses a configuration to move the pair of conveyor frames in the substrate width direction. Hence the opening of the frame can be opened over the entire width. This means that when a printed substrate which requires only the direct view imaging is held, even a printed substrate whose width dimension extends over the entire width of the opening can receive X-ray inspection. Therefore unnecessary restrictions can be eliminated when both the oblique view capturing and the direct view imaging are used, which is a remarkable effect. Furthermore, space is adjusted by moving the pair of conveyor frames respectively. Hence the present invention is advantageous in that the driving time can be reduced compared with the case when one of the conveyor frames is fixed and the other conveyor frame is movable.

BRIEF DESCRIPTION OF THE DRAWINGS

Fis. 16A to 16D are comparison diagrams depicting functional effects of the present invention, where.

DETAILED DESCRIPTION

Preferred embodiments of the present invention will now be described with reference to the accompanying drawings. In the following description, each component of an X-ray inspection device 10 according to an embodiment of the present invention will be described based on a rectangular coordinate system, where the X-axis is a direction in which a target printed substrate W for inspection is conveyed, the Y axis is a substrate width direction which is orthogonal to the X axis in a horizontal plane, and the Z axis is the vertical direction. On the printed substrate W, many electronic components are mounted and electric conduction portions are soldered. The X-ray inspection device 10 according to this embodiment is configured to inspect for the acceptance of a printed substrate W mainly by inspecting each soldered portion of the electronic components.

Figure 1:
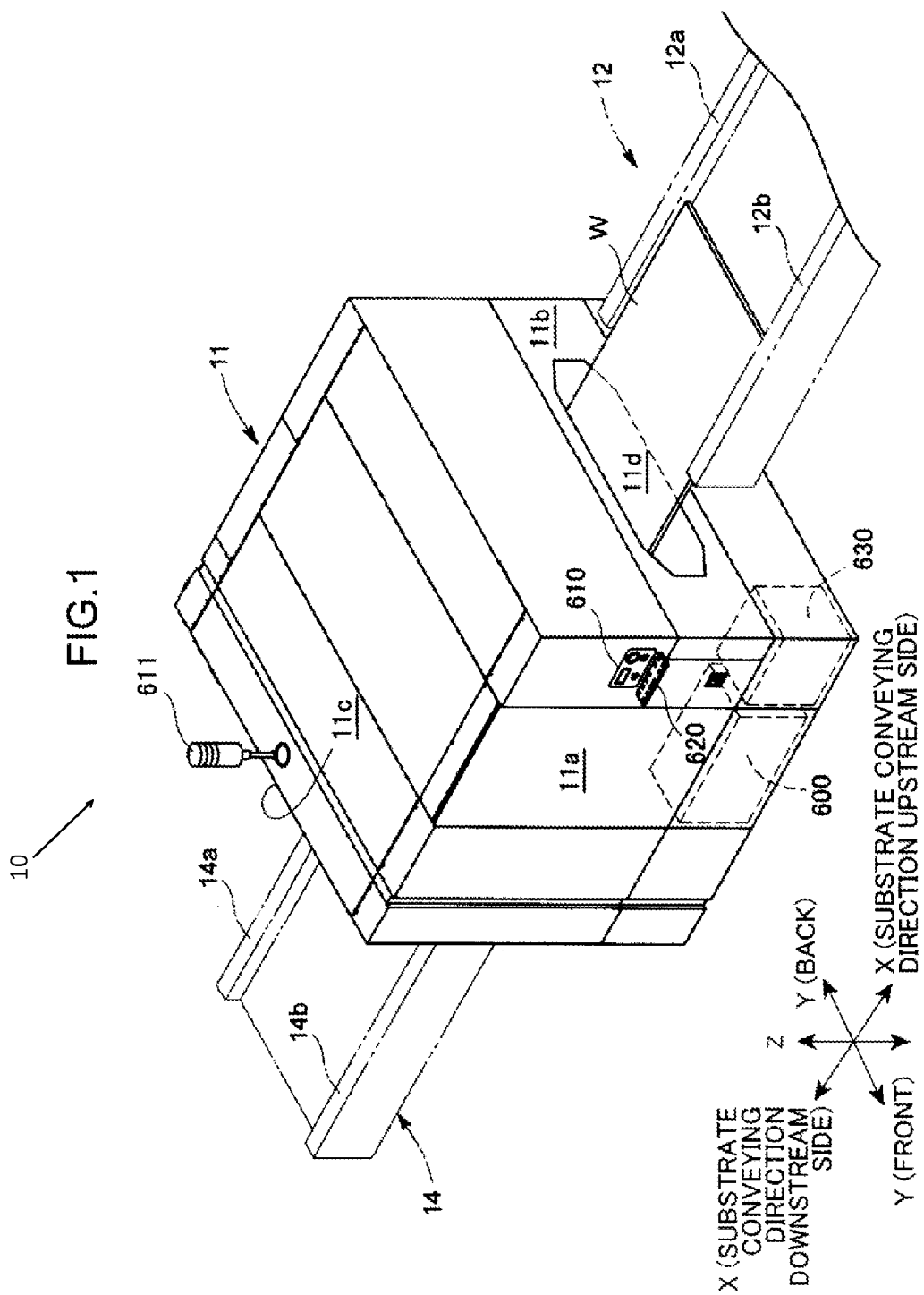
FIG. 1 is a perspective view depicting an appearance of an X-ray inspection device according to an embodiment of the present invention.

As illustrated in FIG. 1, the X-ray inspection device 10 is disposed between a substrate conveyor 12 that carries a board W in after the upstream process is completed, and a substrate conveyor 14 that carries the board W out after the X-ray inspection is completed. The substrate conveyor 12 is formed by a pair of belt conveyors 12a and 12b, and the substrate conveyor 14 is formed by a pair of belt conveyors 14a and 14b. Depending on the specification of the facility where the X-ray inspection device 10 is installed, one of the substrate conveyors 12 and 14 becomes a board carry-in conveyor and the other becomes a board carry-out conveyor. In this example in FIG. 1, it is assumed that the substrate conveyor 12 on the right side is the carry in side, and the substrate conveyor 14 on the left side is the carry-out side.

The X-ray inspection device 10 has a housing 11 shielded by lead or the like. The housing 11 has an approximate cube shape. A front surface 11a of the housing 11 faces one side of the Y axis direction. In a facility where the X-ray inspection device 10 is installed, a printed substrate W carried in from the board carry-in conveyor (substrate conveyor 12) is inspected inside the housing 11, and is then carried out from the X-ray inspection device 10 to the board carry-out conveyor (substrate conveyor 14). On the walls 11b and 11c of the housing 11, which the substrate conveyors 12 and 14 face, a shutter mechanism (not illustrated) is disposed respectively, and a printed substrate W is carried in and out through the board carry in/out ports 11d and 11e (see FIG. 2), which are opened or closed by the pair of shutter mechanisms.

Figure 2:
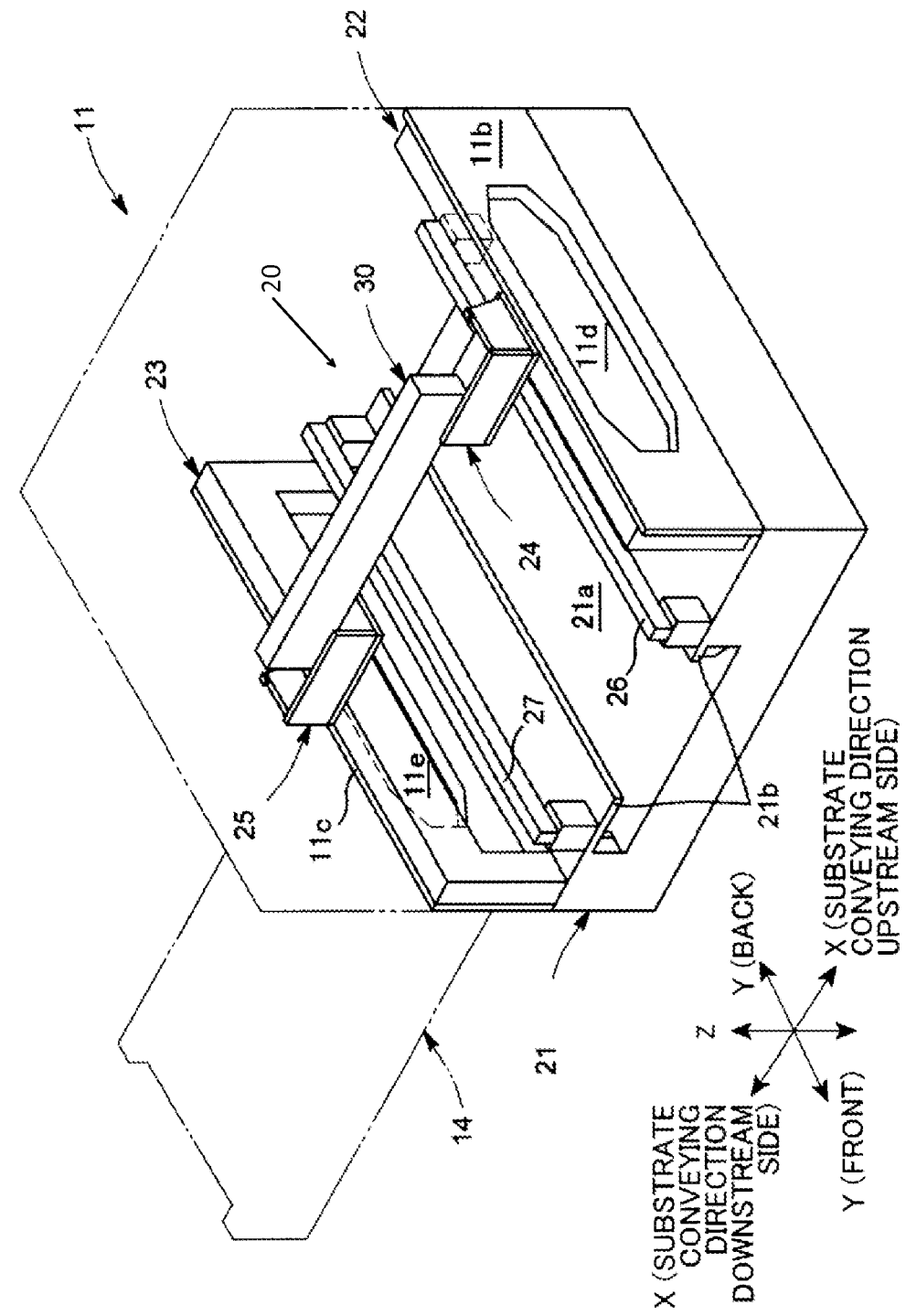
FIG. 2 is a perspective view depicting a structure of the X-ray inspection device in FIG. 1.

As illustrated in FIG. 2, a structure 20 to support each device installed in the X-ray inspection device 10 is constructed inside the housing 11. The structure 20 includes a base 21 which constitutes a bottom portion of the housing 11, a pair of gate portions 22 and 23 which are erected on the base 21, each gate portion respectively reinforces the inner wall portions in the X axis direction, a pair of frame portions 24 and 25 which are respectively fixed to the center portions of the gate portions 22 and 23, and a beam 30 which bridges between the pair of frame portions 24 and 25. Each component of the structure 20 is formed by combining various steel materials and sheet metal members.

A bottom portion 21a is formed on the base 21 such that the center portion with respect to the X axis direction, denting in a rectangular shape, extends along the Y axis direction. A later mentioned X-ray camera unit 40 (see FIG. 3) is installed on the bottom portion 21a. On each side of the bottom portion 21a of the base 21, a shelf portion 21b, which partially protrudes toward the center side in the X axis direction and extends horizontally in the Y axis direction, is integrally provided respectively. On the upper surface of each shelf portion 21b, a Y axis rail 26 (27) that faces the gate portion 22 (23) is disposed respectively. Each Y axis rail 26 (27) constitutes an essential area of a later mentioned table driving mechanism 100. The table driving mechanism 100 includes a movable frame 111. A later mentioned substrate table 60 is placed on the Y axis rails 26 and 27 via the movable frame 111, so as to be movable back and forth along the Y axis rails 26 and 27.

Each gate portion 22 (23) is formed in a gate shape which extends over the corresponding board carry in/out port 11d (11e) of the housing 11, and includes a shutter mechanism (not illustrated) disposed on the corresponding wall 11b (11c) of the housing 11 respectively.

The lower part of each frame portion 24 (25) is welded to the upper part of the corresponding gate portion 22 (23), and the upper surface thereof is welded to each edge of the beam 30 in the X axis direction. The frame portions 24 and 25, together with the gate portions 22, 23 and the beam 30, construct a firm frame structure.

The beam 30 is a structure to support an X-ray irradiation unit 160 as an X-ray source, which is described in detail later (see FIG. 10 to FIG. 12).

Figure 3:
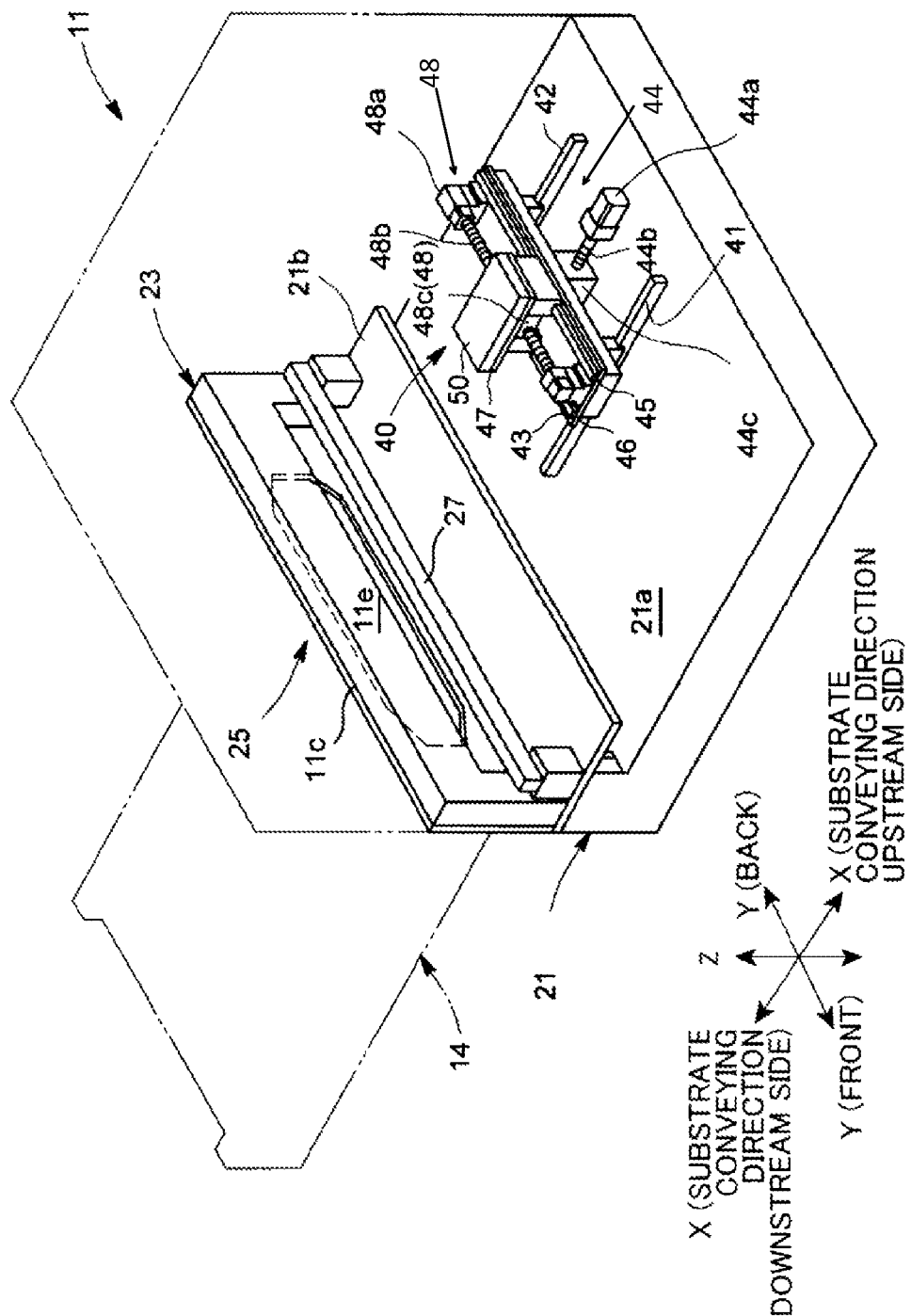
FIG. 3 is a perspective view depicting a general configuration of an X-ray camera unit that is used for the X-ray inspection device in FIG. 1.

As illustrated in FIG. 3, the X-ray camera unit 40 includes: a pair of X axis guide rails 41 and 42 which are disposed in the bottom portion 21a of the base 21, and extend in the X axis direction with a space therebetween in the Y axis direction therebetween; an X axis slide table 43 which is guided on the X axis guide rails 41 and 42 so as to move in the X axis direction; an X axis ball screw mechanism 44 which is disposed in the lower part of the X axis slide table 43 and drives the X axis slide table 43 in the X axis direction; a pair of Y axis guide rails 45 and 46 which are fixed to the upper part of the X axis slide table 43 and extend in the Y axis direction respectively; a Y axis slide table 47 which is guided by the Y axis guide rails 45 and 46 so as to move in the Y axis direction; a Y axis ball screw mechanism 48 which is disposed in the lower part of the Y axis slide table 47 and drives the Y axis slide table 47 in the Y axis direction; and an X-ray camera 50 which is installed on the Y axis slide table 47.

The X axis guide rails 41 and 42 are disposed slightly to the rear in the center area of the bottom portion 21a, and guide the X axis slide table 43 in this position to reciprocate in the X axis direction.

The X axis slide table 43 is formed in a rectangle extending in the Y axis direction in plane view.

The X axis ball screw mechanism 44 includes: an X axis motor 44a installed in the bottom portion 21a; a ball screw 44b which is rotary-driven by the X axis motor 44a; and a nut unit 44c which is screwed into the ball screw 44b and is fixed to the bottom surface of the X axis slide table 43, so that the X axis slide table 43 can reciprocate in the X axis direction by the nut unit 44c, which moves in the X axis direction by the rotation of the ball screw 44b.

The Y axis guide rails 45 and 46 are disposed with a space therebetween in the width direction (X axis direction) of the X axis slide table 43. The Y axis guide rails 45 and 46 extend over approximately the entire length of the X axis slide table 43 in the Y axis direction. The Y axis guide rails 45 and 46 guide the Y axis slide table 47 so that the Y axis slide table 47 reciprocates in the Y axis direction.

The Y axis slide table 47 is a rectangular member which is slightly longer in the X axis direction in planar view. The Y axis slide table 47 supports the X-ray camera 50 on the upper surface thereof. This means that the X-ray camera 50 can move freely in the longitudinal and lateral directions (XY axis directions) on the bottom portion 21a by the movement of the X axis slide table 43 and the Y axis slide table 47. Since the X-ray camera 50 is placed on the Y axis slide table 47, the X-ray camera 50 slightly projects upward from the shelf portion 21b of the base 21.

The Y axis ball screw mechanism 48 includes a Y axis motor 48a installed in a rear end of the X axis slide table 43; a ball screw 48b which is rotary-driven by the Y axis motor 48a; and a nut unit 48c which is screwed into the ball screw 48b and is fixed to the bottom surface of the Y axis slide table 47, so that the Y axis slide table 47 can reciprocate in the Y axis direction by the nut unit 48c, which moves in the Y axis direction by the rotation of the ball screw 48b.

As illustrated in FIG. 4 to FIG. 9, a substrate table 60 includes: a frame 61 which is a main body; a conveyor unit 70 that conveys and supports a printed substrate W on the frame 61; a conveyor driving mechanism 80 that drives substrate conveyors 73 and 74 disposed on the conveyor unit 70; and a distance adjustment mechanism 90 that changes an opposing distance of the conveyor unit 70. In the X-ray inspection device 10 according to this embodiment, a table driving mechanism 100 is also installed in order to drive the substrate table 60 in the X axis direction and the Y axis direction (see FIG. 4, FIG. 10 and FIG. 11).

The frame 61 is connected with the table driving mechanism 100 so as to be movable in the XY axis directions, as described later. As illustrated, the frame 61 is a square frame integrating a pair of X axis pieces 62 and 63 which extend in the X axis direction, and a pair of Y axis pieces 64 and 65 which are disposed on both ends of the X axis pieces 62 and 63, and extend in the Y axis direction, and an opening 66, to transmit X-rays RL, is formed in a square shape in planar view in the center area of the frame 61 (see FIG. 6). The opening 66 has a square shape in planar view enclosed by sides 62a and 63a along the X axis direction (substrate conveying direction) and sides 64a and 65a along the Y axis direction (substrate width direction) such that X-rays transmit through the opening 66.

Figure 8:
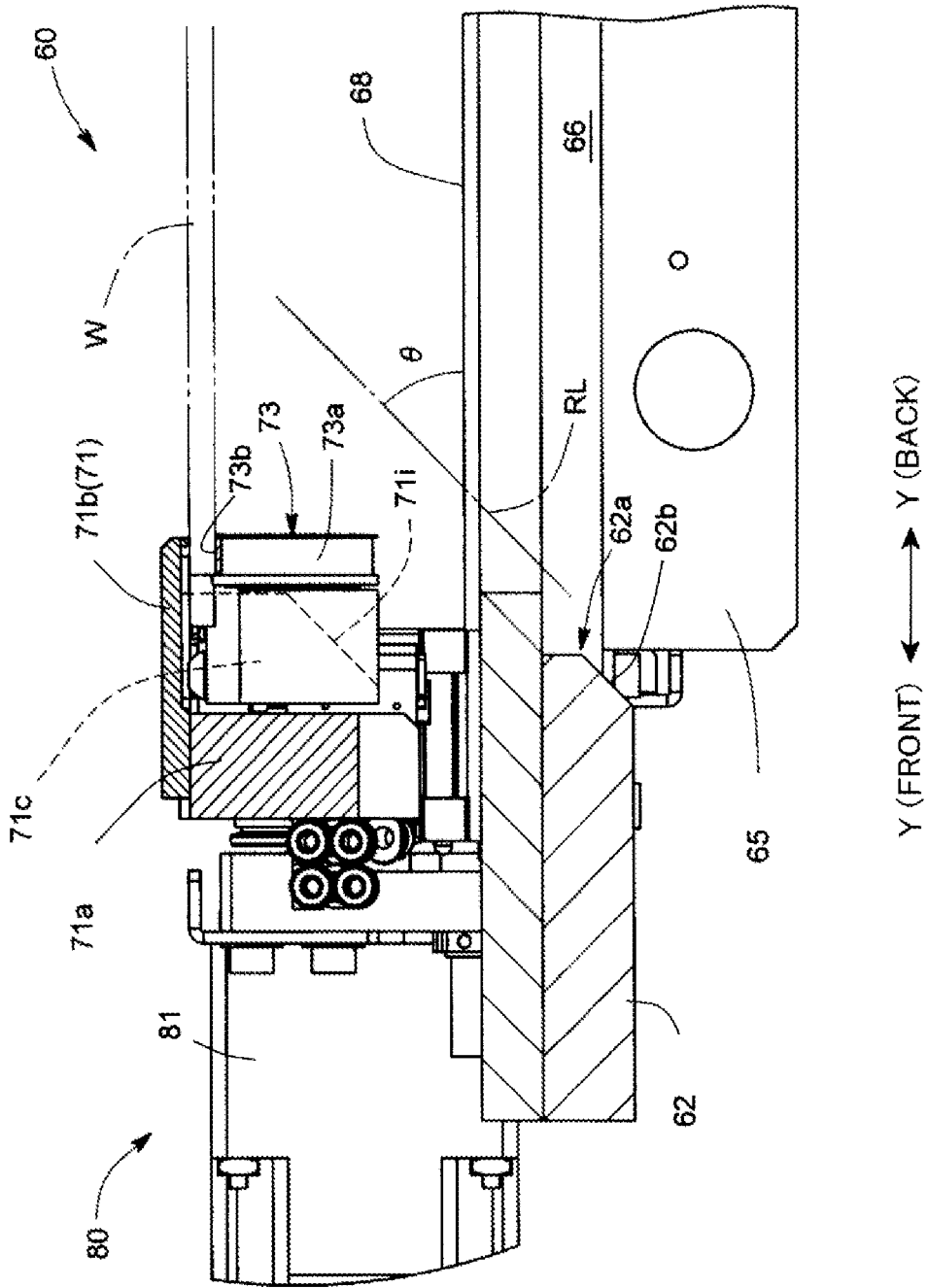
FIG. 8 is an enlarged partial cross-sectional view depicting an essential area of the substrate table in FIG. 4.
Figure 9:
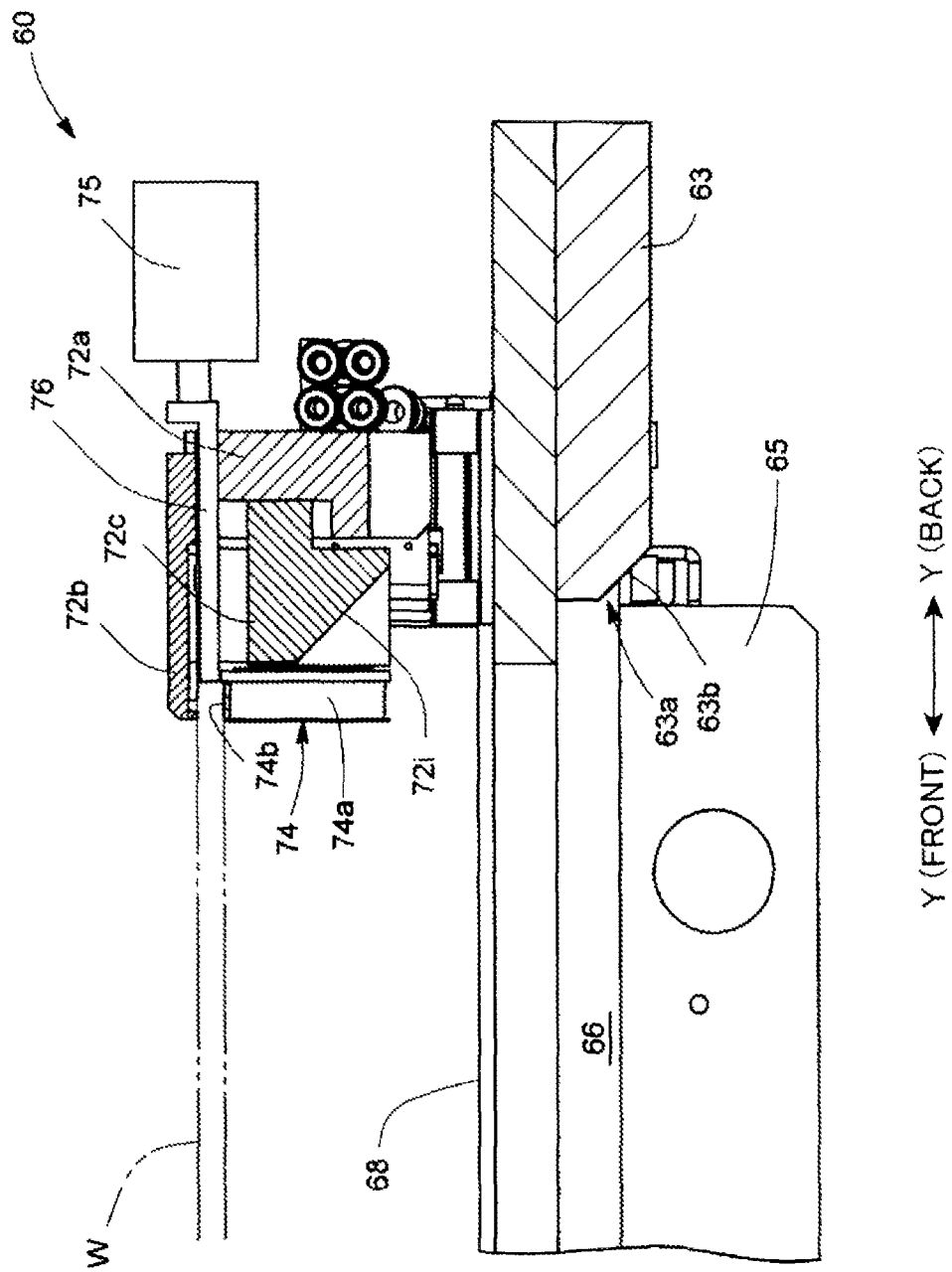
FIG. 9 is an enlarged partial cross-sectional view depicting an essential area of the substrate table in FIG. 4.

In this embodiment, as illustrated in FIG. 8 and FIG. 9, a bevel 62b (63b) is formed in the lower edge of each X axis piece 62 (63) that constitutes the opening 66. The bevel 62b (63b) is formed by chamfering a part of the side 62a (63a) of the opening 66 so that the lower side of the opening 66 becomes wider. By this bevel 62b, an effective opening width of X-rays RL, that transmits at a predetermined elevation angle θ (angle at which X-rays cross with printed substrate W: 45° in the example in FIG. 8) is increased when the oblique view capturing is performed.

Figure 5:
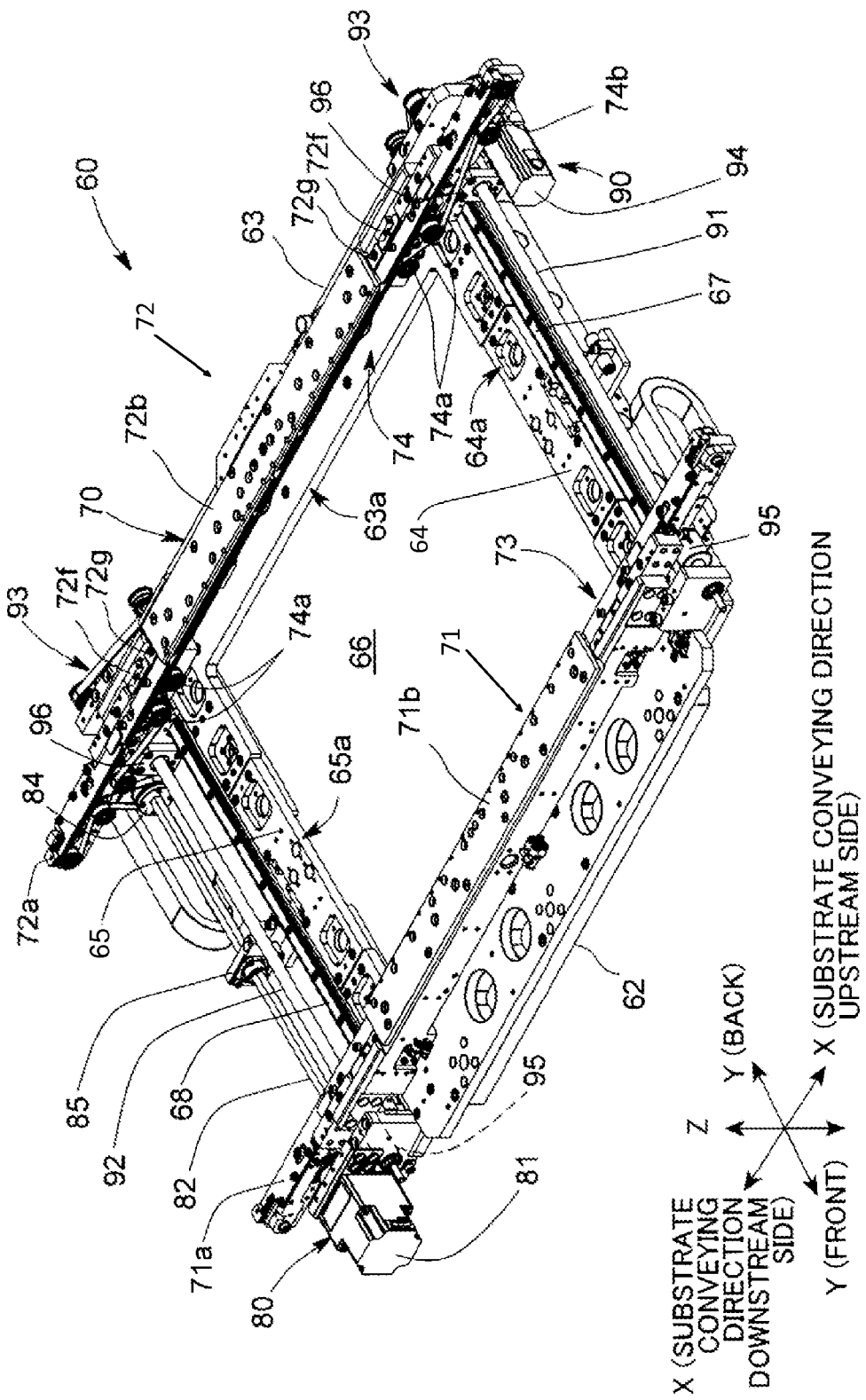
FIG. 5 is an enlarged perspective view of the substrate table in FIG. 4.
Figure 6:
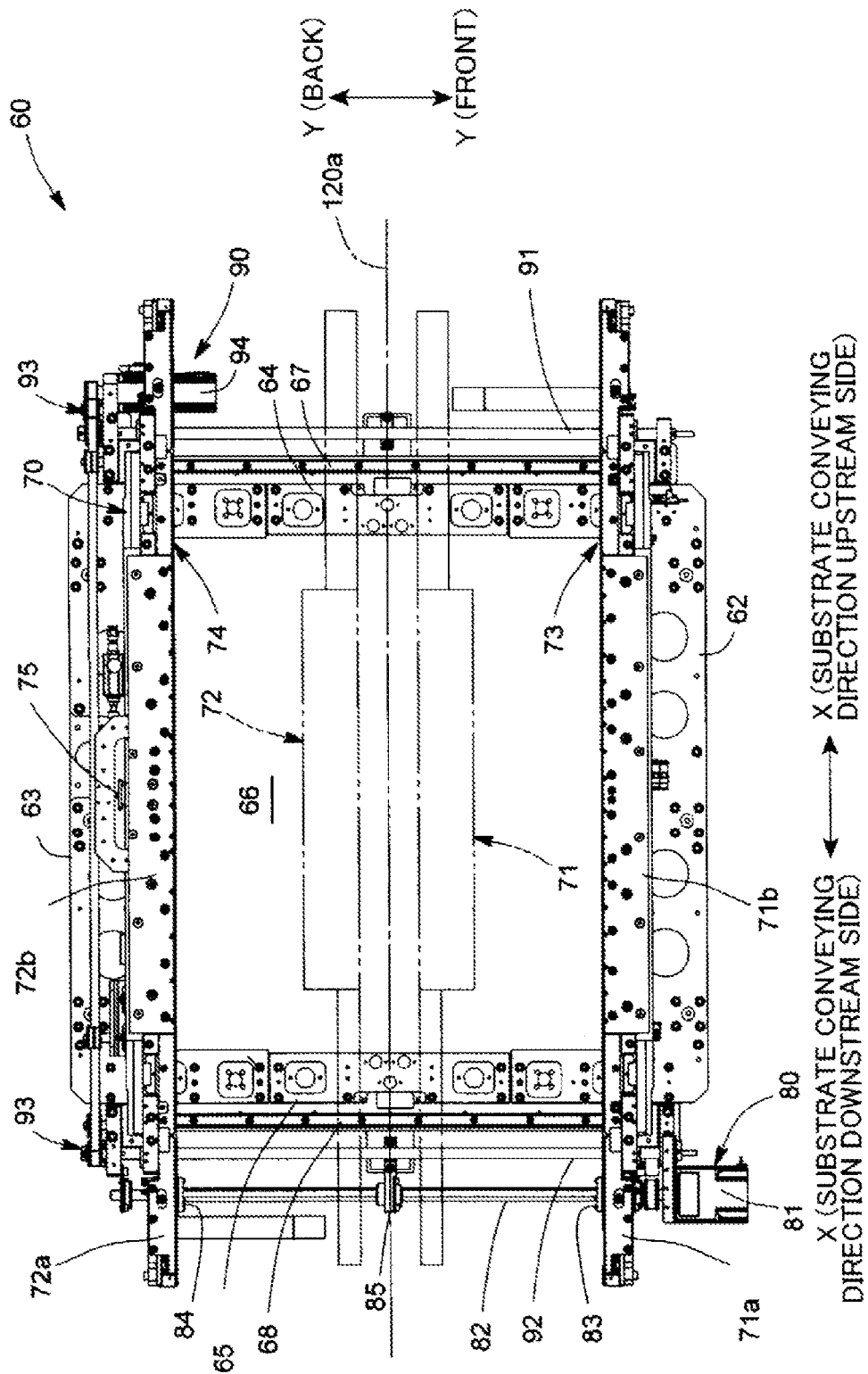
FIG. 6 is a plan view of the substrate table in FIG. 4.

As illustrated in FIG. 5 and FIG. 6, the Y axis rail 67 (68) is fixed to the upper surface of each Y axis piece 64 (65) of the frame 61 respectively. A conveyor unit 70 is mounted on the pair of Y axis rails 67 and 68, and the conveyor unit 70 is constructed to be movable in the Y axis direction on the Y axis rails 67 and 68. In this embodiment, the Y axis rails constitute a part of the distance adjustment mechanism 90 which is described later, and movably connect a pair of conveyor frames 71 and 72 of the conveyor unit 70 to the frame 61 in the Y axis direction respectively.

The conveyor unit 70 includes the pair of conveyor frames 71 and 72 which are disposed on the front and back in the Y axis direction, and a pair of substrate conveyors 73 and 74 disposed on the conveyor frames 71 and 72 respectively.

The conveyor frames 71 and 72 are disposed approximately symmetrically with respect to a center line 120a in the X axis direction that passes through the center of the opening 66 (see FIG. 16A and FIG. 16B), and can clamp a printed substrate W therebetween by moving toward each other in the Y axis direction (see FIG. 6).

As illustrated in FIG. 5 and FIG. 8, each conveyor frame 71 (72) includes: an X axis frame 71a (72a) which extends in the X axis direction and of which edge projects from the frame 61; a pressing plate 71b (72b) which is fixed to the upper surface of the X axis frame 71a (72a) and of which side portion projects to the opening 66 side; a movable member 71c (72c) which clamps a printed substrate W in tandem with the pressing plate 71b (72b); a pair of air cylinders 71d (72d) disposed on both ends of the movable member 71c (72c); a slide member 71e (72e) which is disposed on each air cylinder 71c (72d) and is connected to the cylinder main unit of the air cylinder 71d (72d); and a guide rail 71f (72f) which connects the slide member 71e (72e) to the corresponding X axis frame 71a (72a) so as to be vertically movable.

The X axis frame 71a (72a) is a metal member having a square bar shape, and constitutes a main structure of the conveyor frame 71 (72).

One end of the pressing plate 71b (72b) in the width direction (Y axis direction) is fixed to the upper surface of the X axis frame 71a (72a), and the other end thereof in the width direction (Y axis direction) projects toward the center of the frame 61. The total length (length in the X axis direction) of the pressing plate 71b (72b) is set to be slightly shorter than the total length (length in the X axis direction) of the X axis frame 71a (72a), and the center of the pressing plate 71b (72b) is aligned to the center of the X axis frame 71a (72a).

Each movable member 71c (72c) is disposed under the pressing plate 71b (72b) so as to contact the inner surface side of the corresponding X axis frame 71a (72a). A printed substrate W is conveyed in a state where each end portion of the printed substrate W in the width direction is caught between the movable member 71c (72c) and the pressing plate 71b (72b) respectively, and each end portion of the conveyed printed substrate W in the width direction is clamped/unclamped with the pressing plate 71b (72b) by a vertical motion of the movable member 71c (72c). As illustrated in FIG. 8 and FIG. 9, each movable member 71c (72c) has a facing edge that the movable member 71c (72c) faces in the Y axis direction. On each facing edge, a bevel 71i (72i), which inclines such that a downstream side (lower side in the illustrated example) is wider in the X-ray irradiation direction of the X-ray irradiation unit 160, is formed. These bevels 71i and 72i increase the effective opening diameter when the X-rays transmit through the opening 66.

Each air cylinder 71d (72d) is fixed to each X axis frame 71a (72a) such that a rod thereof projects upward. Each rod of the air cylinder 71d (72d) is connected to the movable member 71c (72c) respectively via a connecting member 71g (72g). Therefore if each air cylinder 71d (72d) is activated, the air cylinder 71d (72d) can vertically move the movable member 71c (72c) via the connecting member 71g (72g).

Each slide member 71e (72e) is integrated with the rod of the air cylinder 71d (72d), and is guided by the guide rail 71f (72f), whereby the movable member 71c (72c) is supported via the air cylinder 71d (72d) so as to freely move vertically.

Each guide rail 71f (72f) is disposed outside the air cylinder 71d (72d) in the X axis direction, and is fixed to the inner surface side of the X axis frame 71a (72a).

The pressing plates 71b and 72b, the movable members 71c and 72c, the air cylinders 71d and 72d and the like, which were described above, constitute a clamp mechanism to clamp a printed substrate W in the illustrated embodiment.

Furthermore, in the illustrated embodiment, an air cylinder 75 and a pressing member 76, which constitute a side clamp, are disposed on one of the conveyor frames (conveyor frame 72 disposed on the rear side in the Y axis direction in the illustrated example), in order to position and secure a printed substrate W to be clamped.

Figure 7:
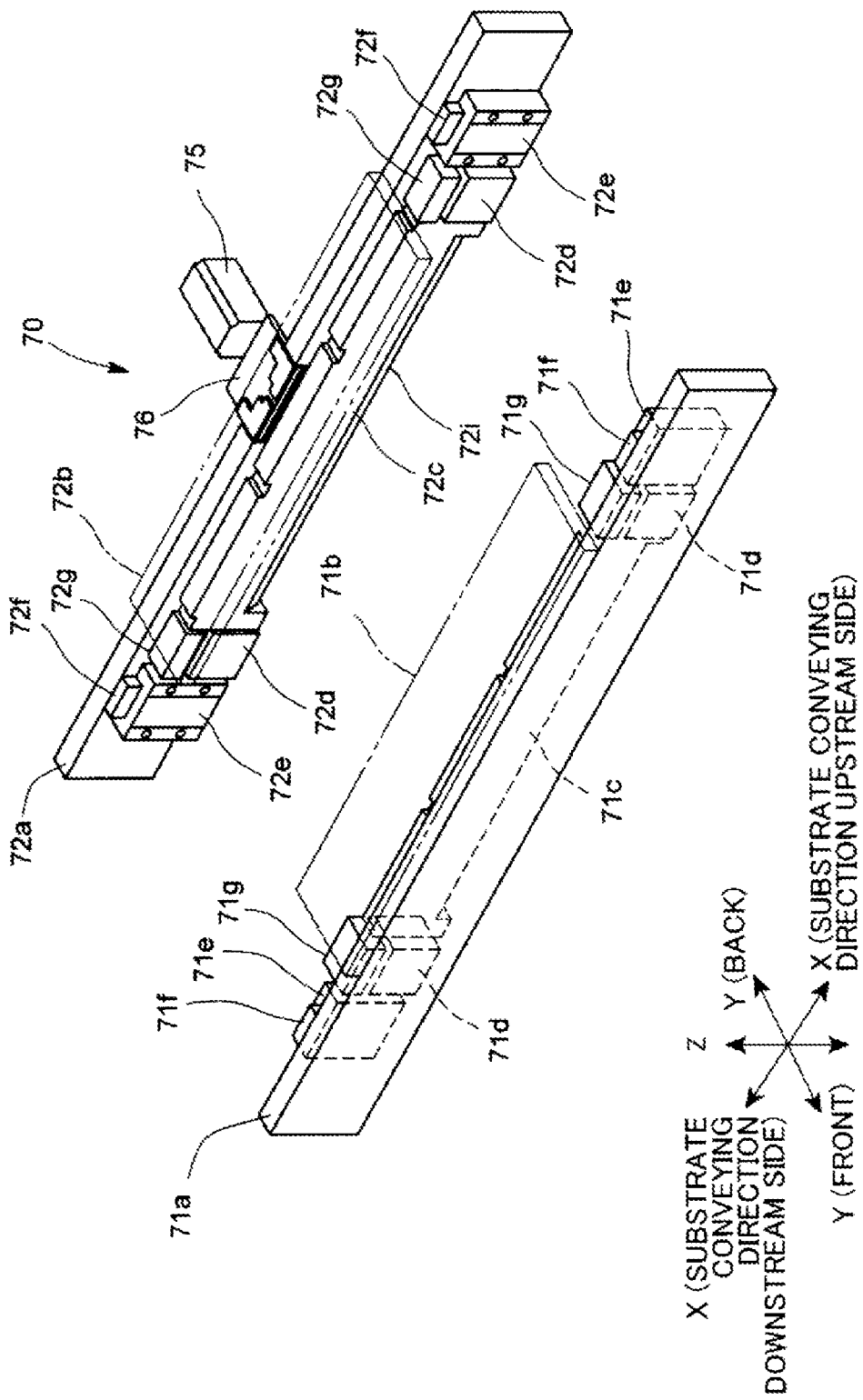
FIG. 7 is a perspective view depicting a clamp mechanism of the substrate table in FIG. 4.

As illustrated in FIG. 7, the air cylinder 75 is integratedly installed on the X axis frame 72a at the rear side of the conveyor frame 72 by a stay (not illustrated). The pressing member 76 is fitted into a notch formed in the center portion of the X axis frame 72a in the X axis direction, so as to reciprocate in the Y axis direction, and can be driven in the Y axis direction by the air cylinder 75. As illustrated in FIG. 9, the pressing member 76 is a thin plate member facing the side portion of a printed substrate W conveyed to an area between the pressing plate 72b and the movable member 72c in the Y axis direction. If the air cylinder 75 is activated and moves the rod forward in FIG. 9, the printed substrate W is pressed forward toward the conveyor frame 71 side, whereby the side portion of the printed substrate W is set along the conveyor frame 71, and can be secured in the width direction in a state where displacement has been corrected. Therefore if the printed substrate W is pressed in the width direction with a predetermined load, and the air cylinders 71d and 72d are activated in this state and the printed substrate W is clamped between the pressing plates 71b and 72b and the movable members 71c and 72c, then the printed substrate W can be secured and accurately positioned in a state where horizontal displacement has been corrected.

Each substrate conveyor 73 (74) is a unit which is installed on a main portion of the air cylinder 71d (72d) and the facing surface of the slide member 71e (72e), and forms the substrate conveying mechanism, along with the conveyor driving mechanism 80. Each substrate conveyor 73 (74) is formed by many rollers 74a disposed along the surface of each conveyor frame 71 (72) which face each other, and a belt 74b wound around each roller 74a. The belt 74b is directly under the pressing plate 71b (72b) in planar view, and contacts the end portion of the printed substrate W in the width direction, which is conveyed between the pressing plates 71b and 72b and the movable members 71c and 72c, so as to convey the printed substrate W. In FIG. 5, the roller and the belt of the substrate conveyor 73 on the front side are not visible, but have the same specifications as the roller 74a and the belt 74b of the substrate conveyor 74 on the rear side.

As illustrated in FIG. 5, the conveyor driving mechanism 80 is a unit that constitutes, along with the substrate conveyors 73 and 74, the substrate conveying mechanism. The conveyor driving mechanism 80 includes: a motor 81 which is installed on one end of the frame 61 in the X axis direction, on the front side in the Y axis direction, and outputs power in a direction around the Y axis; a drive shaft 82 which is disposed between the pair of substrate conveyors 73 and 74 along the Y axis direction, and is rotary-driven around the Y axis by the motor 81; and output pulleys 83 and 84 which are connected to the front side and the rear side of the drive shaft 82 in the Y axis direction (see FIG. 6). The output pulley 83, which is connected to the front side of the drive shaft 82 in the Y axis direction, outputs power to the belt of the substrate conveyor 73. The output pulley 84, which is connected to the rear side of the drive shaft 82 in the Y axis direction, outputs power to the belt 74b of the substrate conveyor 74. The drive shaft 82 driven by the motor 81 is formed to have a polygonal cross-section, and the output pulleys 83 and 84 form a pair, which is connected to the drive shaft 82 so as to be relatively movable along the axis direction of the drive shaft 82 (that is, the Y axis direction), in a state where relative rotation with the drive shaft 82 is restricted. One output pulley 83 (on the front side of the Y axis direction) constitutes a first output pulley which transfers power to one substrate conveyor 73 (on the front side in the Y axis direction). The other output pulley 84 (on the rear side in the Y axis direction) constitutes a second output pulley which transfers power to the other substrate conveyor 74 (on the rear side in the Y axis direction). In the illustrated example, the drive shaft 82 is supported by a bearing 85 installed on the Y axis piece 65 of the frame 61, so that the drive shaft 82 can smoothly rotate.

The distance adjustment mechanism 90 includes: a pair of Y axis rails 67 and 68; a pair of double-end studs 91 and 92 which are disposed on both sides of the conveyor frames 71 and 72 in the X axis direction and extend in the Y axis direction respectively; a power transfer unit 93 which is disposed on the back surface of the rear side conveyor frame 72 and transfers a rotary force in a same direction to the double-end studs 91 and 92; and a motor 94 which is installed on the other end in the X axis direction (upstream side in the substrate conveying direction) of the rear side conveyor frame 72 and outputs rotary force around the Y axis to the power transfer unit 93. In each double-end stud 91 (92), a right screw and a left screw are symmetrically formed with respect to the center in the Y axis direction, and each screw is screwed into a nut mechanism 95 (96) disposed on the conveyor frame 71

(72) respectively. The pair of nut mechanisms 95 installed on one X axis piece 62 (on the front side in the Y axis direction) constitutes a first nut mechanism, which screws into one end (on the front side in the Y axis direction) of the corresponding double-end stud 91 (92) respectively. The pair of nut mechanisms 96 installed on the other conveyor frame 71 (72) (on the rear side in the Y axis direction) constitutes a second nut mechanism, which screws into the other end (on the rear side in the Y axis direction) of the corresponding double-end stud 91 (92) respectively. The output of the motor 94 is transferred to the pair of double-end studs 91 and 92 by the power transfer unit 93, whereby the pair of double-end studs 91 and 92 rotate in a same direction at a same speed. If double-end studs 91 and 92 rotate in one direction (e.g. clockwise), the double-end studs 91 and 92, in tandem with the nut mechanisms 95 and 96, move the conveyor frames 71 and 72 to approach each other, as shown by the virtual line in FIG. 6. If the double-end studs 91 and 92 rotate in the other direction (e.g. counter-clockwise), the double-end studs 91 and 92 move the conveyor frames 71 and 72 to depart from each other, as shown by the solid line in FIG. 6. In this embodiment, by using this mechanism, the conveyor frames 71 and 72 are driven so as to equally approach or depart from each other in the Y axis direction, thereby adjusting a width dimension of the printed substrate W that can be conveyed by the substrate conveyors 73 and 74 as the substrate conveying mechanism disposed on each of the conveyor frames 71 and 72.

Figure 4:
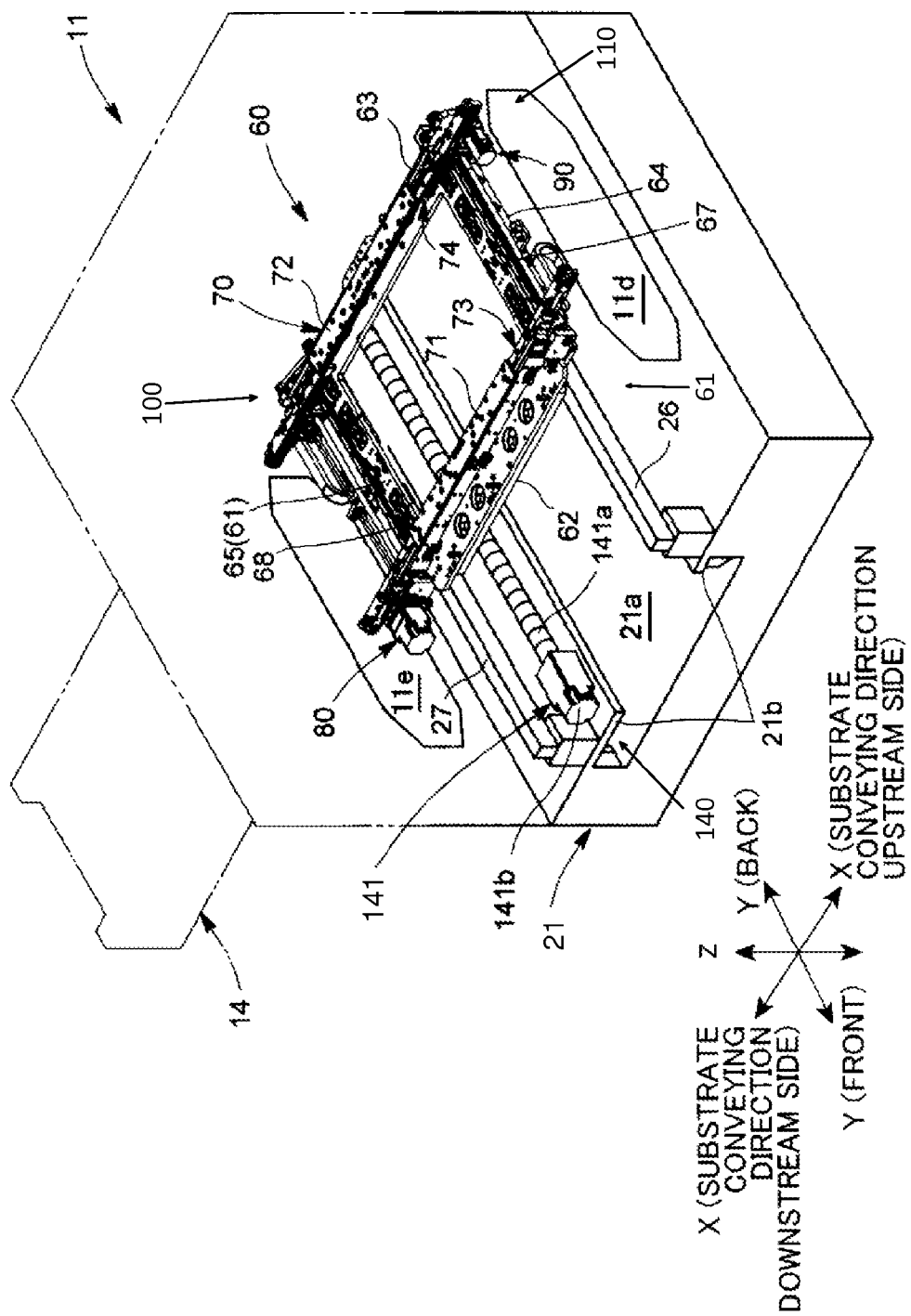
FIG. 4 is a perspective view depicting a general configuration of a substrate table used for the X-ray inspection device in FIG. 1.

As illustrated in FIG. 4 to FIG. 10, the table driving mechanism 100 includes: an X axis drive unit 110 which drives the substrate table 60 in the X axis direction; and a Y axis drive unit 140 which drives the substrate table 60 in the Y axis direction via the X axis drive unit 110 (see FIG. 4).

The X axis drive unit 110 includes: a movable frame 111 which is disposed on the lower surface of the frame 61 of the substrate table 60; a pair of X axis rails 112 and 113 which are disposed on the movable frame 111 with a space therebetween in the Y axis direction and guide the substrate table 60 in the X axis direction; and an X axis ball screw mechanism 114 which is disposed behind the X axis rail 113 on the rear side. The movable frame 111 is a frame-shaped structure of which center is open, as with the frame 61. The X axis ball screw mechanism 114 includes: a ball screw 114a which extends in the X axis direction, a nut portion (not illustrated) which is screwed into the ball screw 114a; and an X axis motor 114b which drives the ball screw 114a around the X axis. The nut portion is fixed to the frame 61 of the substrate table 60. The nut portion receives a rotational force of the ball screw 114a and transfers the force, to relatively move the substrate table 60 in the X direction, to the movable frame 111. This means that if the X axis motor 114b rotates and the ball screw 114a rotates, the substrate table 60 can reciprocate in the X axis direction by the force in the X axis direction received from the nut portion.

As illustrated in FIG. 4, the Y axis drive unit 140 includes: the pair of Y axis rails 26 and 27 disposed on the shelf portion 21b; and the Y axis ball screw mechanism 141 which is disposed inside the Y axis rail 26 on the downstream side in the substrate conveying direction, that is, the X axis direction (the side where the Y axis rail 26 on the downstream side of the substrate conveying direction faces the Y axis rail 27 on the upstream side of the substrate conveying direction in the X axis direction). The Y axis rails 26 and 27 guide the movable frame 111 respectively so as to reciprocate in the Y axis direction. The Y axis ball screw mechanism 141 includes: a ball screw 141a that extends in the Y axis direction; a nut portion (not illustrated) which screws into the ball screw 141a; and a Y axis motor 141b which rotary-drives the ball screw 141a. The ball screw 141a is rotatably supported on the shelf portion 21b by a bearing (not illustrated). The nut portion is fixed to the lower surface of the movable frame 111, receives a rotational force of the ball screw 141a, and transfers the force to drive the substrate table 60 in the Y axis direction via the movable frame 111. This means that if the Y axis motor 141b rotates and the ball screw 141a rotates, the substrate table 60 can reciprocate in the Y axis direction by the force in the Y axis direction received from the nut portion.

Now an X-ray irradiation unit (an example of an X-ray source) 160 for performing transmission inspection on a printed substrate W held on the substrate table 60 will be described. The X-ray irradiation unit 160 is supported by an X-ray source support mechanism 150. First this X-ray source support mechanism 150 will be described.

Figure 11:
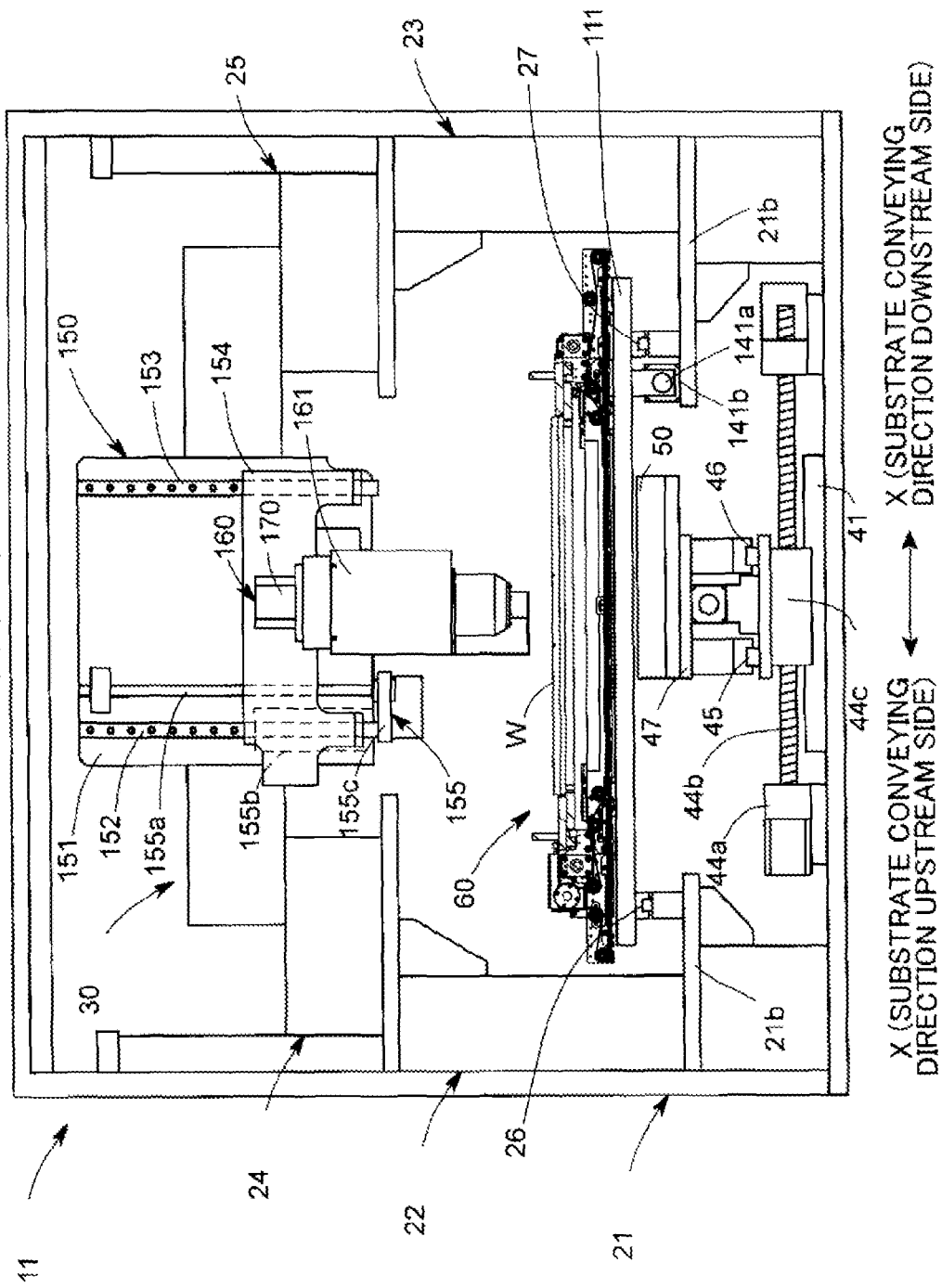
FIG. 11 is a cross-sectional view depicting the back surface side of the X-ray inspection device in FIG. 1.
Figure 12:
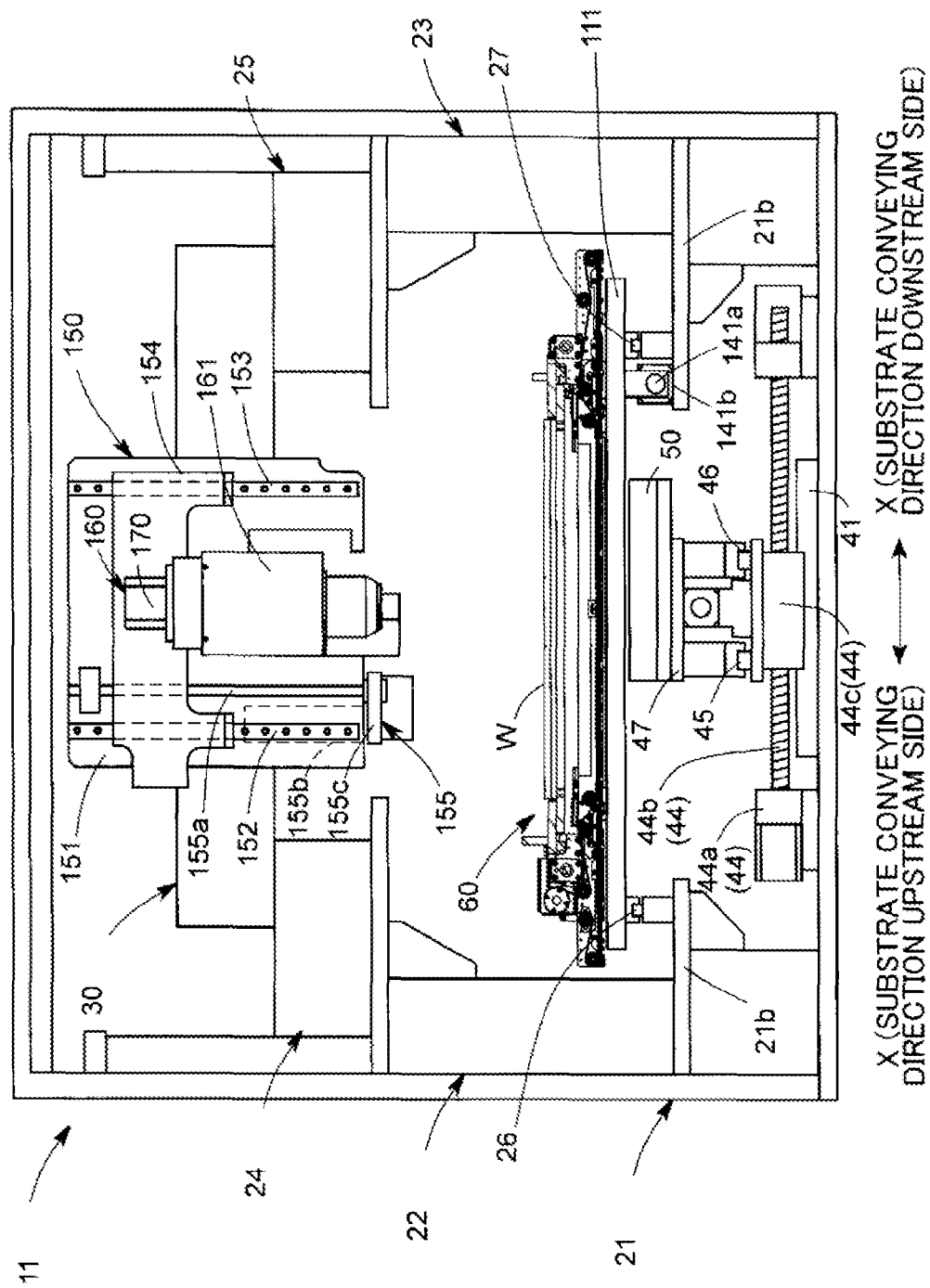
FIG. 12 is a cross-sectional view depicting the back surface side of the X-ray inspection device in FIG. 1.

As illustrated in FIG. 11 and FIG. 12, the X-ray source support mechanism 150 includes: a plate-shaped support plate 151 which is secured to the back surface of the beam 30; a pair of elevating rails 152 and 153 which are fixed to the back surface of the support plate 151 and extend in the Z axis direction; an elevating slider 154 which is connected to the elevating rails 152 and 153; and a ball screw mechanism 155 which vertically drives the elevating slider 154. The support plate 151 is a metal sheet member that constitutes, along with the beam 30, a structure 20, and in the illustrated example, the support plate 151 is firmly secured to the beam 30. A stopper (not illustrated) is disposed in the support plate 151, and the elevating slider 154 is guided so as to be vertically movable in the Z axis direction within a stroke range specified by this stopper. The stroke range is determined based on the predetermined magnification required for the X-ray image of the X-ray inspection device 10.

The magnification will be described with reference to FIG. 17A and FIG. 17B. In the following description, it is assumed that the X-ray irradiation unit 160 is a dotted X-ray source shown in FIG. 17A and FIG. 17B.

The distance L0, from the printed substrate W to the X-ray camera unit 40, is always constant.

The elevating slider 154, on the other hand, directly supports the X-ray irradiation unit 160. If the elevating slider 154 vertically moves along the elevating rails 152 and 153, the X-ray source (X-ray irradiation unit) 160 integrally moves vertically. If the X-ray source (X-ray irradiation unit) 160 moves vertically, the distance L1, from the X-ray source (X-ray irradiation unit) 160 to the printed substrate W held on the substrate table 60, changes. In the same manner, if the X-ray source (X-ray irradiation unit) 160 moves vertically, the distance L2 (=L0+L1) of the reaching path of the X-rays, that are transmitted from the X-ray irradiation unit 160 to the X-ray camera unit 40 via the printed substrate W, also changes. The magnification of the X-ray image captured by the X-ray camera unit 40 is L2/L1=1+(L0/L1). Therefore, if the X-ray source (X-ray irradiation unit) 160 moves integrally, the distances L1 and L2 change, and as a result the magnification changes.

Figure 10:
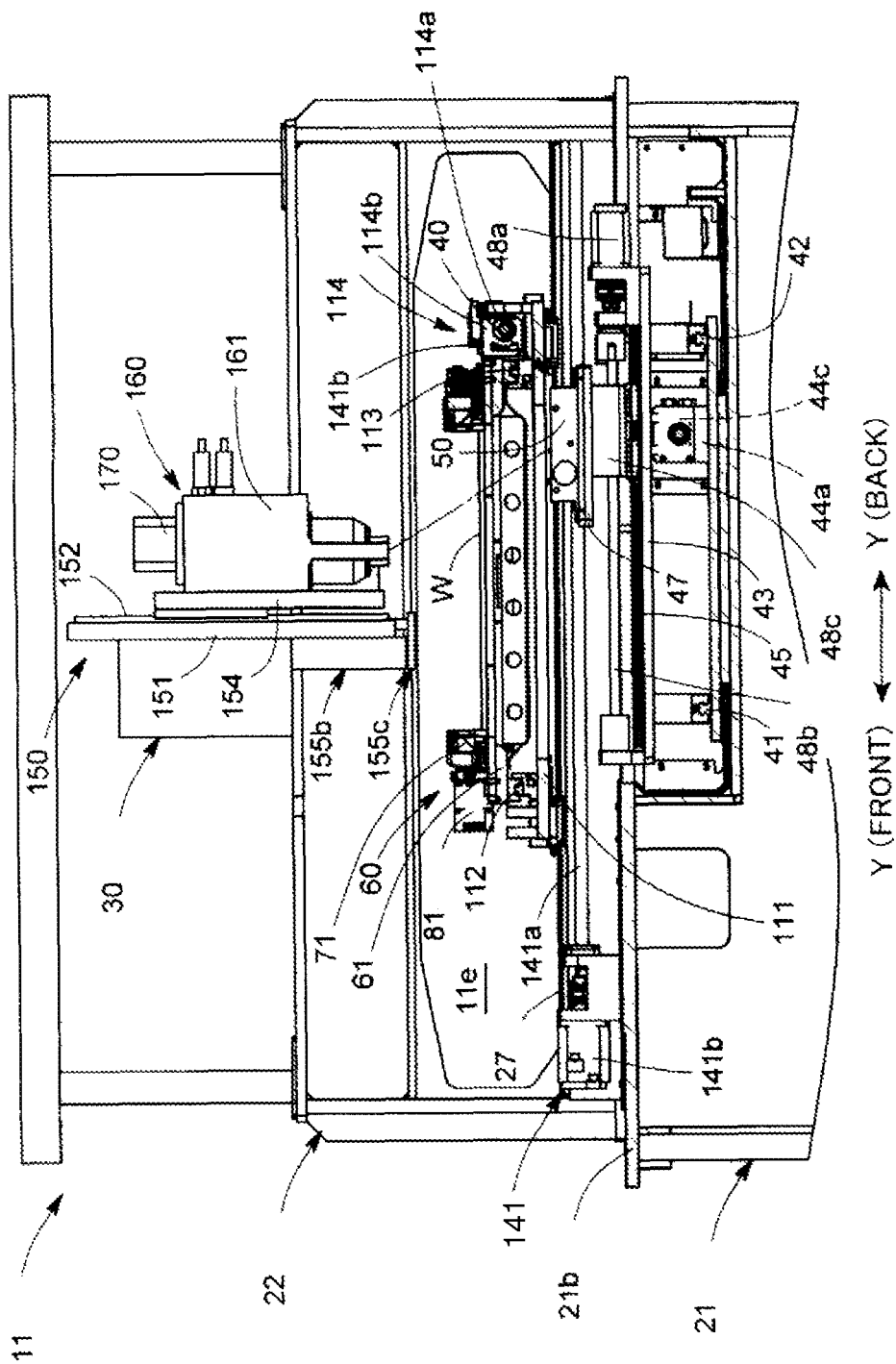
FIG. 10 is a cross-sectional view depicting a downstream side of the X-ray inspection device in FIG. 1 in the substrate conveying direction.
Figure 17A:
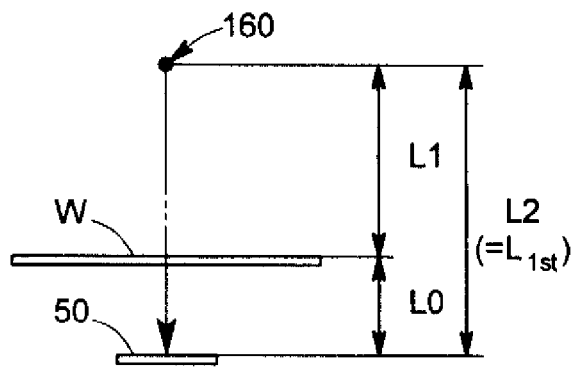
FIG. 17A is a diagram depicting a change of magnification of an X-ray image in a close up position by the X-ray camera unit that is used for a composite inspection device in FIG. 1.
Figure 17B:
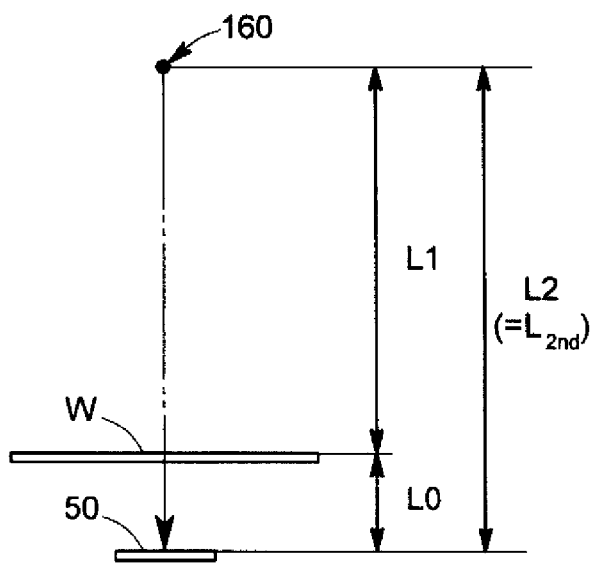
FIG. 17B is a diagram depicting a change of magnification of an X-ray image in a non-close up position by the X-ray camera unit that is used for the composite inspection device in FIG. 1.

As illustrated in FIG. 10 and FIG. 17A, when the X-ray irradiation unit 160 is in the lowered position, the reaching path becomes the first distance $L_{1st}$, and the magnification of the X-ray image becomes a close up magnification, which is larger than the original size. In other words, the X-ray irradiation unit 160 is in the close up position when lowered. As illustrated in FIG. 11 and FIG. 17B, when the X-ray irradiation unit 160 is in the elevated position, the reaching path becomes the second distance $L_{2nd}$, which is longer than the first distance $L_{1st}$. When the X-ray irradiation unit 160 is elevated, the non-close up magnification is a lower magnification in the wider angle than the imaging in the close up position (greater magnification than the original size). In other words, the X-ray irradiation unit 160 is in the non-close up position when elevated. The elevating rails 152 and 153 guide the elevating slider 154 such that the X-ray irradiation unit 160 moves vertically between the close up position and the non-close up position.

On the other hand, the X-ray inspection device 10 of this embodiment is constructed to execute the oblique view capturing, where the X-rays RL are irradiated onto a printed substrate W at a predetermined elevation angle θ, and the essential inspection area is imaged diagonally. In this oblique view capturing, constraints are set in a later mentioned control unit 600 so that the image is always captured at the close up position.

As illustrated in FIG. 11 and FIG. 12, the ball screw mechanism 155 includes: a ball screw 155a which extends in the Z axis direction and is rotatably supported on the back surface of the support plate 151; a nut portion (not illustrated) which is screwed into the ball screw 155a; a Z axis motor 155b which rotary-drives the ball screw 155a around the Z axis; and a belt mechanism 155c that transfers the output of the Z axis motor 155b to the ball screw 155a. The ball screw 155a extends over approximately the entire height of the support plate 151, so that the X-ray irradiation unit 160 can vertically move in the stroke range. The nut portion is fixed to the front surface of the elevating slider 154, and receives the rotational force of the ball screw 155a and transfers the force to move vertically to the elevating slider 154. The Z axis motor 155b is installed on the front surface of the support plate 151 in the Z axis direction with the output axis thereof facing downward. The belt mechanism 155c includes: an output pulley installed on the output axis of the Z axis motor 155b; an input pulley installed at the lower end of the ball screw 155a; and a belt wound around the pulleys, so that the driving force of the Z axis motor 155b is transferred to the ball screw 155a via the pulleys and the belt. In this way, the Z axis ball screw mechanism 155 constitutes a magnification change unit that changes the magnification of the X-ray image, by relatively changing the positions of the X-ray irradiation unit 160 and the X-ray camera 50 between the close up position (see FIG. 11) where the direct distance for the X-rays irradiated from the X-ray irradiation unit 160 to reach the X-ray camera 50 is short for close up imaging, and the non-close up position (see FIG. 12) where the direct distance for the X-rays irradiated from the X-ray irradiation unit 160 to reach the X-ray camera 50 is longer than the distance for the close up position.

In the illustrated example, the X-ray irradiation unit 160 has a housing 161, a high voltage generation unit (not illustrated) which is housed inside the housing, and an X-ray irradiation source that receives power from the high voltage generation unit and irradiates X-rays.

As illustrated in FIG. 11 and FIG. 12, an R axis motor 170 is disposed on top of the X-ray irradiation unit 160. Since the distribution of X-rays irradiated from the X-ray irradiation source is not uniform, the distribution of irradiated X-rays is changed so as to be located around the vertical axis by activating the R axis motor 170, whereby the required essential inspection area is imaged.

Figure 13:
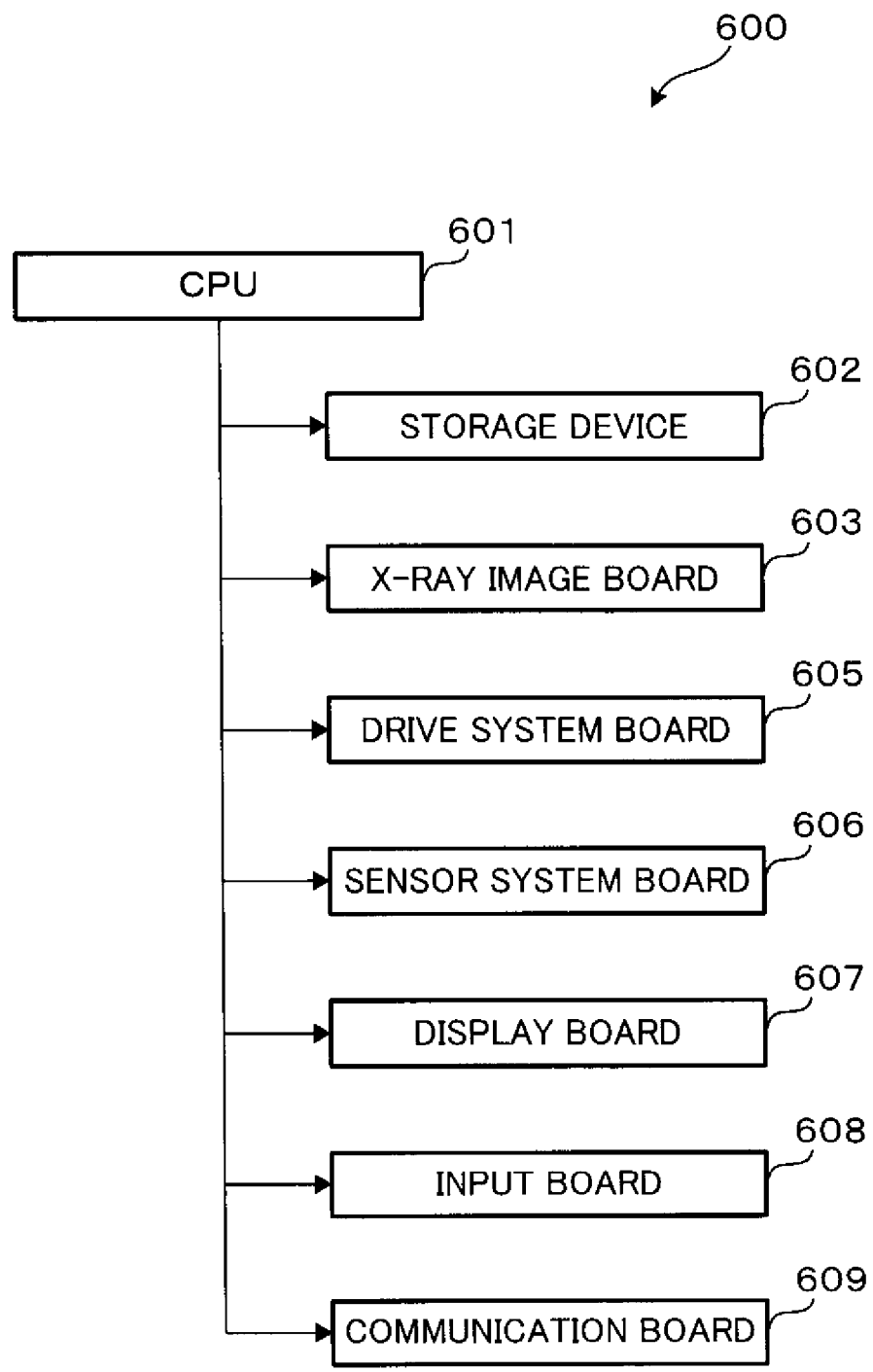
FIG. 13 is a block diagram depicting a control unit of the X-ray inspection device in FIG. 1.

As illustrated in FIG. 1 and FIG. 13, a control unit 600 for controlling the entire device is installed in the X-ray inspection device 10. In this embodiment, a display panel 610 and a keyboard 620 are installed on the front surface of the X-ray inspection device 10. A lamp 611 is erected on top of the X-ray inspection device 10 in order to indicate the operation state. A power supply device 630 is installed on the upstream side of the control unit 600 in the substrate conveying direction.

The control unit 600 has a main control unit (CPU) 601 which is a microprocessor or the like, and a storage device 602, an X-ray image board 603, a drive system board 605, a sensor system board 606, a display board 607, an input board 608, a communication board 609 and the like are connected to the main control unit 601.

The storage device 602 is ROM, RAM, an auxiliary storage device or the like, and stores, for example, programs and master data required for controlling each component of the X-ray inspection device 10 and executing inspection, master data on an inspection target product, such as a printed substrate W to be inspected, surface mounted components and inspection items, and master data defining inspection specifications on the inspection target items.

The X-ray image board 603 is an interface for connecting the X-ray camera 50 and the main control unit 601, and through this X-ray image board 603, the main control unit 601 can execute the transmission inspection of the inspection target product, based on the X-ray images captured by the X-ray camera 50.

The drive system board 605 is an interface for connecting various motors installed in the X-ray inspection device 10 (e.g. respective X axis motors 44a, 141b, 114b, 144b, 155b, 185b of ball screw mechanisms 44, 114, 141, 155 and 185) and an actuator, such as an air cylinder 75, with the main control unit 601, and through this drive system board 605, the main control unit 601 can control the rotation direction, rotation amount, rotation speed, operation timing or the like of various motors, and control the switching operation of each air cylinder 71d, 72d and 75 of the conveyor unit 70.

The sensor system board 606 is an interface for connecting various sensors of the X-ray inspection device 10 with the main control unit 601, and through this sensor system board 606, the main control unit 601 can detect the operation timing of each component and whether or not the printed substrate W is present, based on the detection result detected by these various sensors.

The display board 607 is an interface for connecting the display panel 610, which is installed on the front surface of the X-ray inspection device 10, and the lamp 611 with the main control unit 601, and through the display board 607, the main control unit 601 can display the control information on the display panel 610 as the graphical user interface (GUI), or can flash the lamp 611 disposed on top of the X-ray inspection device 10 (see FIG. 1).

The input board 608 is an interface for connecting a pointing device, such as the keyboard 620 installed on the front surface of the X-ray inspection device 10, with the main control unit 601, and through this input board 608, the main control unit 601 can accept data from the keyboard 620 or the like operated by the user.

The communication board 609 is for executing data communication with a host computer which manages a production program of a facility where the X-ray inspection device 10 is installed, and through this communication board 609, the main control unit 601 is connected with the host computer via LAN and/or WAN, and can acquire information on the inspection target items, such as an item number of the target printed substrate W for inspection.

Based on the programs and other data stored in the storage device 602, the main control unit 601 controls each component of the X-ray inspection device 10 according to the following procedure.

Figure 14:
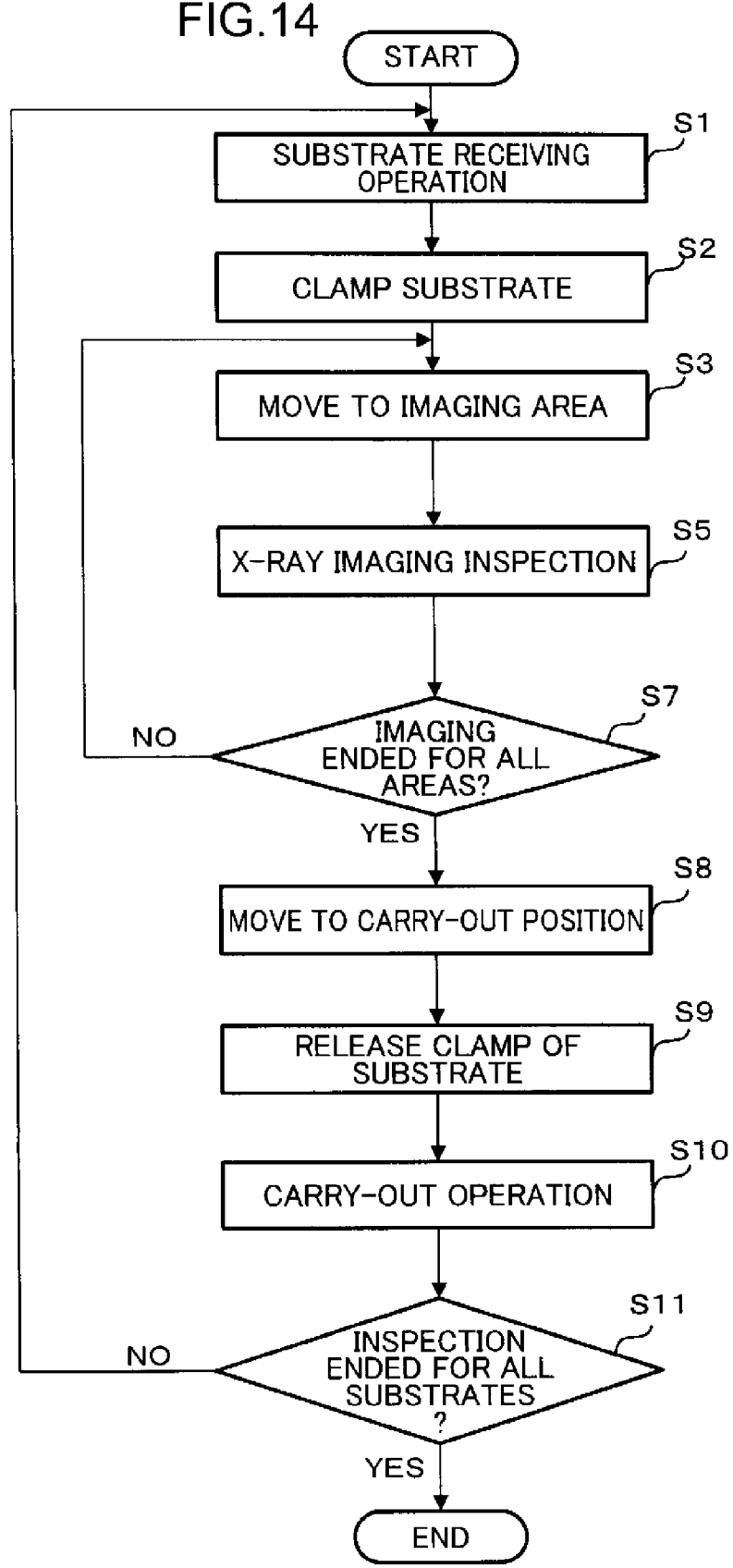
FIG. 14 is a flow chart depicting an inspection operation by the X-ray inspection device in FIG. 1.
Figure 15:
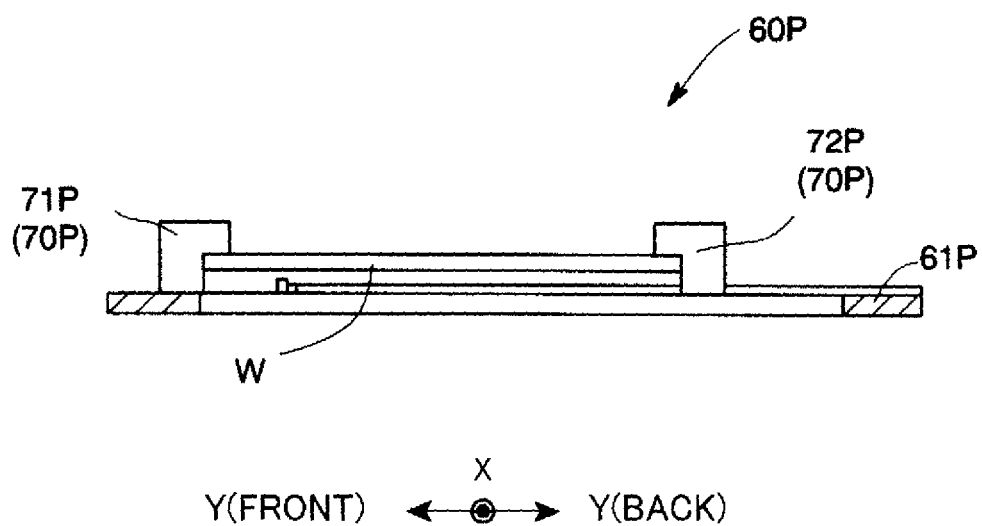
FIG. 15 is a prior art schematic cross-sectional view depicting a general configuration of a substrate table of a prior art.

As illustrated in FIG. 1 and FIG. 14, the main control unit 601 executes a substrate receiving operation (step S1). In the substrate receiving operation, a printed substrate W, which completed the upstream process, is conveyed by the substrate conveyor 12, then the shutter mechanism of the board carry in/out port 11*d* opens to open the board carry in/output port 11*d*, and the printed substrate W is received. At this time, the substrate table 60 is driven by the X axis motor 114*b* of the X axis ball screw mechanism 114, and moves toward the board carry on/output port 11*d*, and receives the printed substrate W carried in by the substrate conveyor 12. If this X-ray inspection device 10 is used in a multi-item small lot production environment, the width dimensions of the printed substrates W to be carried in vary, but according to this carry in/receiving operation, the distance adjustment mechanism 90 of the substrate table 60 is activated and adjusts the space between the pair of conveyor frames 71 and 72 of the conveyor unit 70 to a dimension matching with the width of the printed substrate W to be carried in, based on the communication data acquired from the host computer in advance. The printed substrate W carried in through the board carry in/out port 11*d* is conveyed to the substrate table 60 by the conveyor driving mechanism 80 of the conveyor unit 70. After being carried in, the shutter mechanism on the carry in side is activated and the board carry in/out port 11*d* closes again, so that X-rays will not leak during X-ray imaging.

The printed substrate W, which was carried in and moved to a predetermined position, is clamped and held between the pair of conveyor frames 71 and 72 of the conveyor unit 70 by the clamp mechanism of the conveyor unit 70 (step S2).

When the printed substrate W is clamped, the substrate table 60 is driven by the X axis motor 114*b* of the X axis ball screw mechanism 114 again, and moves to a predetermined position inside the X-ray inspection device 10 (step S3). Thereby the printed substrate W is set in the inspection position. Along with the movement of the substrate table 60, the X axis motor 44*a* and the Y axis motor 48*a* of the camera unit 40 are activated respectively for X-ray imaging, so as to move the X-ray camera 50 to a predetermined imaging position. In the X-ray irradiation unit 160, the R axis motor 170 is driven in advance as required.

Then the main control unit 601 executes the X-ray imaging inspection (step S5). In the X-ray imaging inspection, the main control unit 601 executes the direct view inspection and the oblique view inspection, which are combined according to the inspection item of the essential inspection area of the printed substrate W. In the oblique view inspection, the X-ray irradiation unit 160 is moved to the close up position, and each of the ball screw mechanisms 44 and 48 of the X-ray camera unit 40 is activated, as illustrated in FIG. 10, whereby the X-ray camera 50 is moved to a position corresponding to the elevation angle of the X-ray RL. In this state, the main control unit 601 activates the X-ray camera 50 and captures an oblique view X-ray image, and executes transmission inspection based on the captured image. The inspection result is stored in an auxiliary storage of the storage device 602.

Then the main control unit 601 determines whether imaging is completed in all of the areas (step S7). If an un-imaged area remains, the main control unit 601 returns to step S3, and repeats the above mentioned processing. In this embodiment, in some cases both X-ray imaging with a wide angle at a non-close up position and close up X-ray imaging at a close up position must be executed for a same essential inspection area, therefore in the determination in step S7, the main control unit 601 returns to step S3 and repeats the above mentioned processing, assuming that an un-imaged area remains until all the required imaging inspections end for the same area.

When imaging completes in all the areas, the main control unit 601 executes processing to move the printed substrate W after the inspection to the carry out position (step S8). In this carry out movement operation, the X axis drive unit 110 of the table driving mechanism 100 is activated again, and drives the substrate table 60 to the downstream side in the substrate conveying direction along the X axis direction (direction to approach the board carry in/out port 11*e* in the illustrated example, see FIG. 2). When the substrate table 60 faces the board carry in/out port 11*e* on the carry out side, and the movement of the substrate table 60 stops, the clamp of the substrate table 60 is released (step S9) and the carry out operation is executed (step S10). In the carry out operation, the shutter mechanism on the carry out side is activated and opens the board carry in/out port 11*e*. Then the conveyor driving mechanism 80 activates the substrate conveyors 73 and 74 and carries out the inspected printed substrate W to the substrate conveyor 14 on the carry out side. After carry out, the shutter mechanism is activated. The shutter closes the board carry in/out port 11*e*, to shift to the next operation. The X axis drive unit 110 of the table driving mechanism 100 is activated again, and drives the substrate table 60 to the upstream side in the substrate conveying direction along the X axis direction (direction to approach the board carry in/out port 11*d* in the illustrated example, see FIG. 2).

After the carry out operation S10, the main control unit 601 determines whether inspection is completed for all the printed substrates W (step S11). If there is an unprocessed printed substrate W, the main control unit 601 returns to step S1, and repeats the processing described above, and if the inspection completes for all the printed substrates W, processing ends.

Figure 16A:
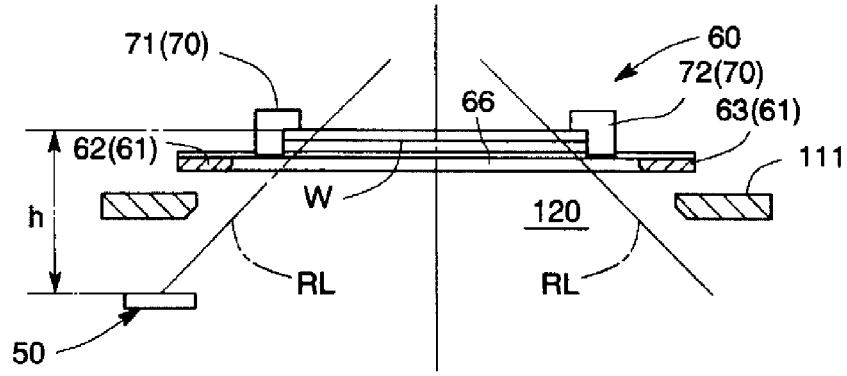
FIG. 16A is a schematic cross-sectional view depicting a case of inspecting a small width printed substrate according to the present embodiment.
Figure 16B:
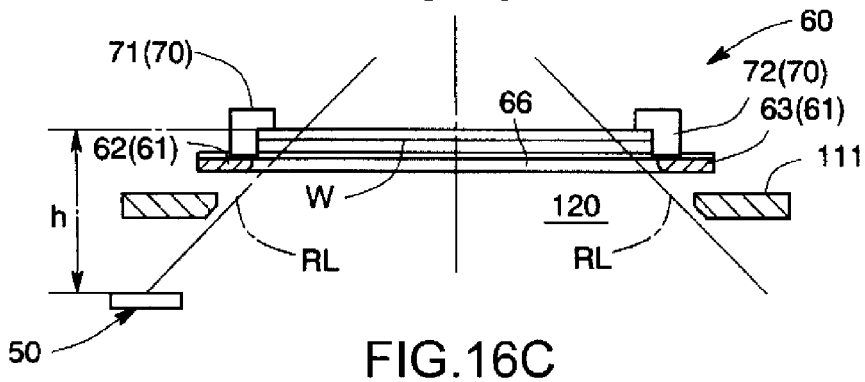
FIG. 16B is a schematic cross-sectional view depicting a case of inspecting a large width printed substrate according to the present embodiment.
Figure 16C:
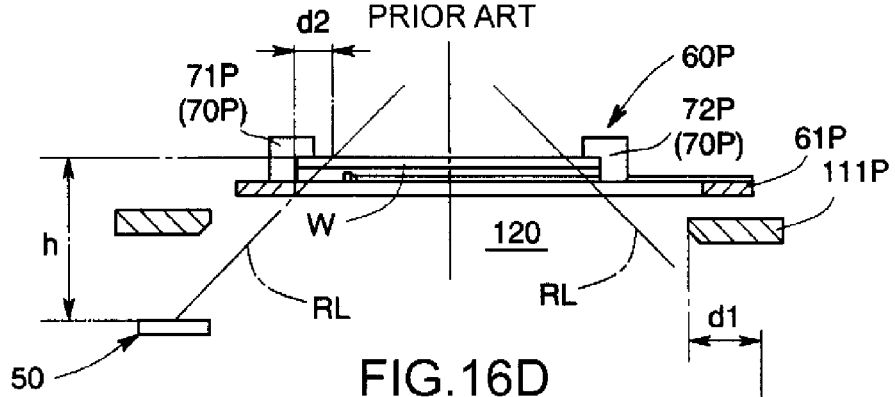
FIG. 16C is a prior art schematic cross-sectional view depicting a case of inspecting a small width printed substrate when the prior art in FIG. 15 is used.
Figure 16D:
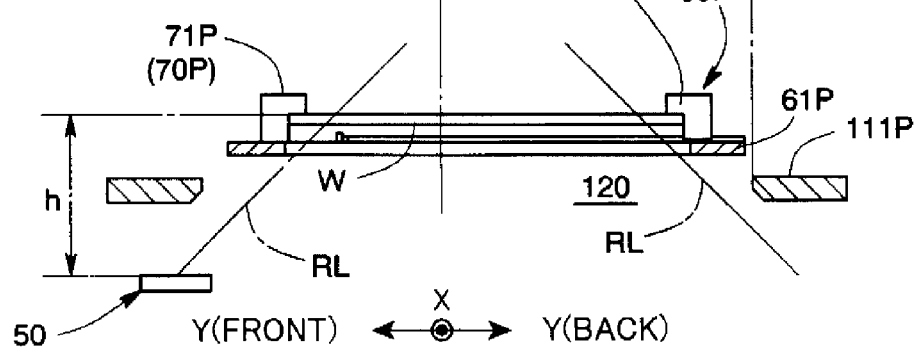
FIG. 16D is a prior art schematic cross-sectional view depicting a case of inspecting a large width printed substrate when the prior art in FIG. 15 is used.

In the X-ray inspection processing described above, particularly at a facility which performs multi-item small lot production, printed substrates W having various width dimensions are conveyed and receive X-ray inspection by the X-ray inspection device 10. In this case, the substrate table 60 activates the distance adjustment mechanism 90 and drives each conveyor frame 71 and 72 of the conveyor unit 70, corresponding to the width of the target printed substrate W for inspection, but according to this embodiment, the pair of conveyor frames 71 and 72 are disposed symmetrically with respect to the opening 66 of the frame 61, and the distance adjustment mechanism 90 equally drives the pair of conveyor frames 71 and 72 to approach or depart from each other in the Y axis direction, hence as illustrated in FIG. 16A and FIG. 16B, each of the conveyor frames 71 and 72 equally opens the opening 66 in the width direction of the printed substrate W while maintaining the symmetry with respect to the center line 120*a* along the X axis direction (substrate conveying direction) of the opening 66. This means that the center line 120*a*, that bisects the width direction of the printed substrate W, can be matched with the center line 120*a* of the opening 66, and therefore when the oblique view capturing is executed for a printed substrate W held on the substrate table 60, an increase in the frame size (generation of dimension d1 shown in FIG. 16C and FIG. 16D), which occurs when the substrate table 60P of Japanese Patent Application Laid-open No. 2003-315288 is used, can be prevented. Furthermore, a configuration to symmetrically move the pair of conveyor frames 71 and 72 with respect to the frame 61 is used, hence the opening 66 of the frame 61 can be opened extending over the entire width. When a printed substrate W which requires only the direct view imaging is held, even a printed substrate W whose width extends over the entire width of the opening 66 can receive the X-ray RL inspection. Further, the space is adjusted by equally moving the conveyor frames 71 and 72, hence the driving time can be reduced (to ½ if the driving speed is the same) compared with a case when one of the conveyor frames 71 (72) is fixed and the other conveyor frame 72 (71) is movable. Moreover, the center line that bisects the width direction of the printed substrate W can be matched with the center line of the opening 66, which makes centering with the opening 66 for transmitting X-rays easier.

In this embodiment, as illustrated in FIG. 5, FIG. 8 and FIG. 9, the frame 61 has four sides 62a, 63a, 64a and 65a that form the opening 66 to a square in planar view, and at least two sides 62a and 63a in the X axis direction, out of the sides 62a, 63a, 64a and 65a, have a bevel 62b (63b) which inclines such that the downstream side in the X-ray irradiation direction of the X-ray irradiation unit (lower side in this example) is wider. Therefore according to this embodiment, the path of the X-rays RL can be opened using the bevels 62b and 63b when the oblique view capturing is performed, whereby the oblique view capturing becomes possible for a wider printed substrate W.

In this embodiment, in particular, each of the pair of conveyor frames 71 and 72 has a facing edge that the conveyor frame faces in the Y axis direction, and a bevel 71i (72i), which inclines such that the downstream side in the X-ray irradiation direction of the X-ray irradiation unit is wider, is formed on the facing edge. Therefore according to this embodiment, a wider effective opening diameter for X-rays to transmit through the opening 66 can be secured by the bevels 71i and 72i, whereby the oblique view capturing becomes possible for an even wider printed substrate W.

In this embodiment, as illustrated in FIG. 5 and FIG. 6, the distance adjustment mechanism 90 includes: the double-end studs 91 and 92 which extend in the Y axis direction and of which screw directions at one end and at the other end being set to be opposite; the first nut mechanism 95 which is installed in one of the conveyor frames 71 (72) and is screwed into one end of the double-end stud 91 (92); the second nut mechanism 96 which is installed in the other conveyor frame 72 (71) and is screwed into the other end of the double-end stud 91 (92); the motor 94 for driving each of the double-end studs 91 and 92; and the power transfer unit 93 which transfers power of the motor 94 to the pair of double-end studs 91 and 92 in a same direction at a same speed. In this embodiment, if the motor 94 is activated, the torque is transferred to each of the double-end studs 91 and 92 at the same time in the same direction via the power transfer unit 93. If the double-end studs 91 and 92 rotate in one direction (e.g. clockwise), the nut mechanisms 95 and 96, which are screwed into the double-end studs 91 and 92, transfer a force to the corresponding conveyor frames 71 and 72 in directions for the conveyor frames 71 and 72 to approach or depart from each other. If the double-end studs 91 and 92 rotate in the other direction (e.g. counterclockwise), the nut mechanisms 95 and 96, which are screwed into the double-end studs 91 and 92, transfer a force to the corresponding conveyor frames 71 and 72 in directions to move the conveyor frames 71 and 72 in the opposite directions from above. Therefore the pair of conveyor frames 71 and 72 can be simultaneously driven using the single motor 94, whereby the drive system can be simplified and the number of components can be decreased.

In this embodiment, the substrate conveying mechanism includes the pair of substrate conveyors 73 and 74 and the conveyor driving mechanism 80 that drives the substrate conveyors 73 and 74, and the conveyor driving mechanism 80 includes the motor 81, the drive shaft 82 that is rotary-driven by the motor 81, and the first output pulley 83 and the second output pulley 84 which form a pair and are movably disposed in the axis direction of the drive shaft 82 in a state where rotation thereof around the axis of the drive shaft 82 is restricted, the first output pulley 83 transferring the power to one of the substrate conveyors 73 (74) and the second output pulley 84 transferring the power to the other substrate conveyor 74 (73). Therefore in this embodiment, the drive shaft 82 is rotated by the rotation of the motor 81. The torque thereof is transferred to the substrate conveyors 73 and 74 via the first and second output pulleys 83 and 84 respectively. Therefore, the substrate conveyors 73 and 74 are simultaneously driven by the single motor 81 in a same direction. The first and second output pulleys 83 and 84 form a pair, so as to be movable in the axis direction of the drive shaft, in a state where the rotation around the axis of the drive shaft is restricted respectively. Hence the power can be transferred to each of the substrate conveyors 73 and 74 without interrupting the displacement of the conveyor frames 71 and 72 by the distance adjustment mechanism 90.

The present invention is not limited to the embodiments described above, but numerous modifications can be made without departing from the true spirit and scope of the invention.

For example, when an oblique view image is captured, the X-ray camera 50 can image at a position relatively displaced from the non-close up position toward the close up position, and need not be relatively displaced to the close up position with exactness.

In this embodiment, the X-ray camera 50 is disposed below the substrate table 60 and the X-ray irradiation unit 160 is disposed above the substrate table 60, but the X-ray camera 50 may be disposed above the substrate table 60 and the X-ray irradiation unit 160 below the substrate table 60.

In this embodiment, the X-ray irradiation unit 160 is vertically moved by the X-ray source support mechanism 150, but the X-ray irradiation unit 160 may be fixed to a predetermined position and the X-ray camera 50 may be driven in the Z axis direction.

The bevels at the edges which mark out the opening of the frame may be formed in the Y axis pieces 64 and 65, instead of the X axis pieces 62 and 63 as described above.

A configuration where the X-ray irradiation unit is disposed below the substrate table and the X-ray camera is disposed above the substrate table may be used.

When the oblique view capturing is performed, a configuration of fixing the X-ray camera and moving the X-ray irradiation unit may be used. Alternatively, a configuration of moving both the X-ray camera and the X-ray irradiation unit may be used.

Moreover, an optical camera may be used as well, so that the appearance inspection and the X-ray inspection are executed simultaneously.

Needless to say, various other modifications can be made within the scope of the claims of the present invention.

INDUSTRIAL APPLICABILITY

The present invention can be applied to an inspection technology field for inspecting essential inspection areas of precision components using X-rays.

The invention claimed is:

1. An X-ray inspection device that is used on a conveyance path for conveying a printed substrate in a predetermined substrate conveying direction, comprising:
a substrate table configured to hold the printed substrate;
an X-ray source configured to irradiate X-rays onto the printed substrate held on the substrate table;
an X-ray camera unit facing the X-ray source across the substrate table, the X-ray camera unit includes an X-ray camera that captures an X-ray image of the printed substrate held on the substrate table, the X-ray camera unit enabling the X-ray camera to move along a plane relative to the X-ray source so as to execute an oblique view capturing taken by diagonally capturing an essential inspection area, upon irradiating X-rays at a predetermined elevation angle onto the substrate;

a frame forming a main body of the substrate table, the frame having an opening to transmit X-rays;

a pair of conveyor frames configured to clamp the printed substrate with respect to a substrate width direction which is orthogonal to the substrate conveying direction in a horizontal plane;

a pair of substrate conveyors, each substrate conveyor being disposed on a respective pair of the conveyor frames, the pair of substrate conveyors forming a substrate conveying mechanism configured to convey a printed substrate supported by the pair of conveyor frames in the substrate conveying direction;

a distance adjustment mechanism configured to drive the pair of conveyor frames so that each of the pair of conveyor frames approaches or departs from each other in the substrate width direction, thereby adjusting a width dimension for allowing a printed substrate to be conveyed by the substrate conveying mechanism;

a movable frame being disposed on a lower surface of the frame; and a table driving mechanism including the movable frame, the table driving mechanism being configured to drive the substrate table via the movable frame in a horizontal direction that is orthogonal to the substrate conveying direction, wherein the distance adjustment mechanism is configured to drive the pair of conveyor frames such that the conveyor frames equally approach or depart from each other, the pair of conveyor frames is disposed on the frame symmetrically with respect to a center axis of the opening along the substrate conveying direction, and the movable frame has a frame structure of which a center is open similarly to the frame, and each of the pair of conveyor frames has a facing edge that the conveyor frame faces in the substrate width direction, and a bevel, which inclines such that a downstream side in an X-ray irradiation direction of the X-ray irradiation unit is wider, and is formed on the facing edge.

2. The X-ray inspection device according to claim 1, wherein
the frame has four sides forming the opening of a square in planar view, and, out of the four sides, at least sides along the substrate conveying direction have a bevel inclining such that a downstream side in an X-ray irradiation direction of the X-ray irradiation unit is wider.

3. The X-ray inspection device according to claim 1, wherein
the distance adjustment mechanism includes:
double-end studs extending in the substrate width direction, screw directions of each double-ends stud at one end and at the other end being set to be opposite;
a first nut mechanism installed in one of the conveyor frames, the first nut mechanism being screwed into one end of the double-end studs;
a second nut mechanism installed in the other conveyor frame, the second nut mechanism being screwed into other end of the double-end studs;
a motor configured to drive the double-end studs; and
a power transfer unit configured to transfer power of the motor to both the double-end studs in a same direction at a same speed.

4. The X-ray inspection device according to claim 1, wherein
the substrate conveying mechanism further includes a conveyor driving mechanism configured to drive the pair of substrate conveyors,
the conveyor driving mechanism includes a motor, a drive shaft rotary-driven by the motor, and a first output pulley and a second output pulley connected to the drive shaft, and
the first output pulley and the second output pulley are connected with the drive shaft such that rotation of the first output pulley and the second output pulley is restricted and the first output pulley and the second output pulley are movable with respect to an axis direction of the drive shaft, the first output pulley transferring power to one of the substrate conveyors and the second output pulley transferring power to the other substrate conveyor.

* * * * *